United States Patent
Yick et al.

(10) Patent No.: US 10,123,854 B2
(45) Date of Patent: Nov. 13, 2018

(54) SELF-LIGATING ORTHODONTIC BRACKET WITH POSITIVE ROTATION LOCK

(71) Applicant: 3M INNOVATIVE PROPERTIES COMPANY, St. Paul, MN (US)

(72) Inventors: Lee C. Yick, Placentia, CA (US); Todd I. Oda, Torrance, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 26 days.

(21) Appl. No.: 15/323,522

(22) PCT Filed: Jul. 8, 2015

(86) PCT No.: PCT/US2015/039578
§ 371 (c)(1),
(2) Date: Jan. 3, 2017

(87) PCT Pub. No.: WO2016/007646
PCT Pub. Date: Jan. 14, 2016

(65) Prior Publication Data
US 2017/0143454 A1    May 25, 2017

Related U.S. Application Data

(60) Provisional application No. 62/022,521, filed on Jul. 9, 2014.

(51) Int. Cl.
*A61C 3/00* (2006.01)
*A61C 7/28* (2006.01)
*A61C 7/30* (2006.01)

(52) U.S. Cl.
CPC ............... *A61C 7/285* (2013.01); *A61C 7/30* (2013.01)

(58) Field of Classification Search
CPC .................. A61C 7/285; A61C 7/30
See application file for complete search history.

(56) References Cited

U.S. PATENT DOCUMENTS

| 3,748,740 A | * | 7/1973 | Wildman | ............... A61C 7/285 |
| | | | | 433/11 |
| 4,536,154 A | | 8/1985 | Garton, Jr. | |

(Continued)

FOREIGN PATENT DOCUMENTS

| EP | 1836990 | 9/2007 |
| JP | 2004-255190 | 9/2004 |

(Continued)

OTHER PUBLICATIONS

International Search Report for PCT International Application No. PCT/US2015/039578, dated Oct. 16, 2015, 4 pages.

*Primary Examiner* — Nicholas Lucchesi

(57) ABSTRACT

The present disclosure provides self-ligating orthodontic brackets with improved control over access to the archwire slot. Access to the archwire slot is controlled by a latch assembly featuring a door rotatable about an axis relative to the bracket body and a lock positioned near the axis to prevent inadvertent rotation of the door. The lock engages a surface of the door and is capable of preventing undesired rotation between an open state, where an archwire is insertable into the archwire slot, and a closed state, where access to the slot is prohibited. The self-ligating brackets may also include a biasing spring to provide active ligation and further inhibit undesired rotation of the door.

16 Claims, 10 Drawing Sheets

(56) References Cited

U.S. PATENT DOCUMENTS

| | | | |
|---|---|---|---|
| 5,078,596 A | 1/1992 | Carberry | |
| 5,254,002 A | 10/1993 | Reher | |
| 5,908,293 A | 6/1999 | Voudouris | |
| 6,648,638 B2 | 11/2003 | Castro | |
| 7,025,591 B1 * | 4/2006 | Kesling | A61C 7/285 433/10 |
| 7,695,277 B1 | 4/2010 | Stevens | |
| 8,282,392 B2 | 10/2012 | Hilliard | |
| 8,469,704 B2 | 6/2013 | Oda | |
| 2002/0034715 A1 * | 3/2002 | Hanson | A61C 7/282 433/11 |
| 2002/0110775 A1 | 8/2002 | Abels | |
| 2004/0013995 A1 * | 1/2004 | Spencer | A61C 7/285 433/11 |
| 2004/0157186 A1 | 8/2004 | Abels | |
| 2005/0019719 A1 | 1/2005 | Hanson | |
| 2005/0186525 A1 | 8/2005 | Abels | |
| 2006/0084025 A1 | 4/2006 | Abels | |
| 2007/0224569 A1 * | 9/2007 | Oda | A61C 7/285 433/10 |
| 2008/0241782 A1 | 10/2008 | Abels | |
| 2009/0170049 A1 * | 7/2009 | Heiser | A61C 7/285 433/11 |
| 2009/0233252 A1 | 9/2009 | Cinader, Jr. | |
| 2009/0325118 A1 | 12/2009 | Lewis | |
| 2010/0285421 A1 * | 11/2010 | Heiser | A61C 7/14 433/11 |
| 2011/0081622 A1 * | 4/2011 | Mashouf | A61C 7/14 433/10 |
| 2012/0064476 A1 * | 3/2012 | Sabilla | A61C 7/285 433/11 |
| 2013/0022935 A1 * | 1/2013 | Ramos-de-la-Pena | A61C 7/16 433/10 |
| 2014/0141384 A1 | 5/2014 | Hagelganz | |
| 2014/0212828 A1 * | 7/2014 | Falcone | A61C 7/14 433/11 |
| 2014/0272751 A1 * | 9/2014 | Cosse | A61C 7/02 433/9 |
| 2015/0182307 A1 * | 7/2015 | Yick | A61C 7/125 433/9 |
| 2017/0086948 A1 * | 3/2017 | Von Mandach | A61C 7/285 |

FOREIGN PATENT DOCUMENTS

| | | |
|---|---|---|
| WO | WO 2011-091397 | 7/2011 |
| WO | WO 2014-018298 | 1/2014 |

* cited by examiner

SELF-LIGATING ORTHODONTIC BRACKET WITH POSITIVE ROTATION LOCK

CROSS REFERENCE TO RELATED APPLICATIONS

This application is a national stage filing under 35 U.S.C. 371 of PCT/US2015/039578, filed Jul. 8, 2015, which claims the benefit of U.S. Provisional Application No. 62/022,521, filed Jul. 9, 2014, the disclosure of which is incorporated by reference in its/their entirety herein.

BACKGROUND

Orthodontic appliances are devices used in the professional supervision, guidance and correction of a patient's malpositioned teeth. The many benefits of orthodontic treatment include the attaining and maintaining of a proper bite function, enhancement of facial aesthetics, and easier maintenance of dental hygiene. Orthodontic appliances are placed in mechanical engagement with the patient's teeth and apply gentle mechanical forces that gradually move the teeth toward corrected positions to achieve a proper bite (or occlusion).

A very common type of orthodontic treatment uses tiny slotted appliances called orthodontic brackets, which are adhesively attached to either the front or back surfaces of the patient's teeth. To move the teeth within an upper or lower arch, a resilient arch-shape wire ("archwire") is mechanically engaged, or "ligated," into the slot of each bracket. The ends of the archwire are generally captured in appliances called molar tubes, which are bonded to the patient's molar teeth. As the archwire slowly returns to its original shape, it acts as a track that guides the movement of teeth toward their desired positions. The brackets, tubes, and archwire are collectively known as "braces."

Conventional brackets are ligated to the archwire with the help of opposing tiewings, which are cleat-like projections on the bracket body. After the archwire is placed in the archwire slot, either a tiny elastomeric "O"-ring ligature or a metal ligature wire is looped over the archwire and beneath the undercut portions of tiewings located on opposite sides of the archwire slot. By tightly encircling the undercut portions of the tiewings, the ligature (or ligature wire) can secure the archwire within the archwire slot of each bracket, while still allowing the archwire to slide longitudinally along the slot. Depending on the relative sizes and shapes of the archwire and the slot, it is possible to achieve a precise mechanical coupling between the two bodies. This enables the practitioner to control the position and orientation of each individual tooth in the arch.

Both of the ligating mechanisms above have certain drawbacks. For example, the frictional contact between O-ring ligatures and the archwire can increase resistance to archwire sliding within the slot. Moreover, the elastic properties of these ligatures can degrade over time, resulting in unpredictable sliding mechanics. While these ligatures can be made from translucent polymers for aesthetic treatment, these same ligatures also tend to stain in the presence of dark-colored foods and liquids. Ligature wire poses its own problems, since the process of tying and trimming the wire can be cumbersome and time-consuming for the orthodontic professional. Being made of metal, ligature wire is also considered non-aesthetic.

Self-ligating brackets present a solution to at least some of the above problems. These appliances generally use a clip, spring member, door, shutter, bail, or other ligation mechanism built into the bracket itself to retain the archwire in the slot, thereby obviating use of a separate ligature. Several advantages can derive from the use of these ligation mechanisms. For example, these appliances can decrease friction between the archwire and the bracket compared with appliances ligated with elastomeric ligatures, potentially providing faster leveling and aligning of teeth in early stages of treatment. Depending on the mechanism, these appliances can also simplify the installation and removal of an archwire, significantly reducing chair time for the treating professional. Finally, self-ligating brackets can provide better hygiene than conventional brackets, which use elastomeric ligatures and ligature wires that can trap food and plaque.

Aesthetic self-ligating appliances, particularly those made from ceramic materials, are also generally "passive" ligation devices. In passive ligation, the archwire is held captive within the slot but allowed to "float" freely within the archwire slot. Passive self-ligating brackets have a slot depth sufficiently large such that a continuous force seating the archwire into the slot is not exerted. Such a configuration can provide low friction between archwire and appliance but the freedom of movement within the archwire slot can compromise control. By contrast, in "active ligation," the appliance imparts a continuous force urging the archwire toward the bottom wall or side wall of the slot. Active ligation can be desirable in some stages of treatment, particularly when using square and rectangular archwires, because "actively" seating these wires into the bracket slot can improve transmission of torque and rotational forces to the teeth. Still other brackets are engineered to be either active or passive, depending on the size and configuration of the archwire.

SUMMARY

In planning an orthodontic treatment, a practitioner often desires to exercise precise control over degree of coupling between bracket and archwire. Self-ligating brackets that use a rigid, sliding door-type mechanism are often passive in nature, particularly when the door has a fixed position relative to the slot. The fixed position of the door relative to the slot can also limit the array of archwire geometries that may be efficaciously ligated. Other self-ligating brackets use a springy and resilient "U"-shaped clip to provide for active ligation. These mechanisms, however, have their own disadvantages. For example, these appliances generally require a higher facial-lingual profile to accommodate both "legs" of the U-shaped clip. Additionally, repeatedly sliding the mechanism open and closed can impart a moment to one leg of the clip, which can permanently deform the clip over time.

Other known self-ligating brackets rely on rotatable doors to control access to the archwire slot. Such doors are commonly pivotable about a hinge axis located on a gingival side of the bracket body. The rotation of such a door to an open configuration can greatly increase the labial-lingual height of the bracket, with an edge or apex of the door positioned near the patient's oral soft tissues. Moreover, such doors are prone to inadvertently transition between an open and closed state, disrupting the ligation process or the course of orthodontic treatment. Certain rotatable door brackets include locking mechanisms on the occlusal side of the archwire slot opposite the hinge axis to prevent undesired transition, but these can be difficult for a treating practitioner to engage or disengage as desired. Consequently, there is need for a self-ligating appliance capable of providing active or passive ligation without the associated disadvantages of existing ligation mechanisms.

The present disclosure provides self-ligating orthodontic brackets with improved control over access to the archwire slot. Access to the archwire slot is controlled by a latch assembly featuring a door rotatable about a hinge axis relative to the bracket body and a lock positioned proximate the axis to prevent inadvertent rotation of the door. Placement of the lock on the same side of the archwire slot as the axis of door rotation renders the latch assembly considerably easier to open. Moreover, the door can be designed to include an appreciable section that is located in a gingival direction from the hinge axis when the bracket is assembled. Locating a substantial portion of the door gingival to the hinge axis may be particularly advantageous, as the arc about which the door must rotate away from the archwire slot to allow entry is reduced to a smaller radius, thereby providing a lower facial-lingual profile for the bracket as it opens. The smaller arc can accordingly reduce interference between the door and adjacent oral tissue, as well as allow treatment of otherwise crowded occlusions.

The lock of the present disclosure is uniquely capable of serving at least two functions, separately or in combination. The lock minimizes or prevents rotation of the door towards the archwire slot while the door is in an open configuration, keeping the door from obscuring access to the archwire slot as long as the lock is engaged. This dramatically reduces the risk to the practitioner of the door inadvertently closing during seating of the archwire. Similarly, the lock minimizes or prevents inadvertent opening of the door when the archwire is secured in the archwire slot during treatment. The latch assembly of the present disclosure accordingly grants dynamically enhanced control over access to the archwire slot. Notably, the self-ligating brackets of the present disclosure do not require a clip or other latching mechanism for securing the door to the body proximate the archwire slot during treatment. The interaction of lock with the door is alone sufficient to arrest the rotation of the door in the desired state.

The self-ligating brackets of the present disclosure can also include a spring that exerts a bias on the door to enable active ligation of an archwire seated in the archwire slot. The spring is located on the same side of the archwire slot as the hinge axis and engages a cam or other structure on the door to bias the door in the direction of a lingual wall of the archwire slot. The door is configured to engage the spring at multiple positions about the hinge axis. So long as there is some contact between the cam or other door structure and the spring, the door will be capable of applying active force in the desired direction. This configuration allows the brackets of the present disclosure to provide more precise active ligation for an enhanced range of archwire geometries. In addition to the potential benefits of active ligation, the spring can provide additional insurance, in cooperation with a locking structure, against unwanted opening or closing of the door.

In one aspect, the present disclosure provides a self-ligating orthodontic appliance comprising a base for bonding the appliance to a tooth surface and a body extending outwardly from the base, the body defining an archwire slot extending in a mesial-distal direction across the body. A hinge structure defining a first reference axis is disposed on a first side of the archwire slot. A door is coupled to the hinge and is rotatable about the first reference axis between an open state and a closed state. The door includes a lingual surface and is connected to the hinge structure. An archwire is insertable into the archwire slot in the open state and the door retains the archwire in the archwire slot in the closed state. A locking mechanism engages the door, impeding rotation of the door to the open state when the door is in the closed state. The locking mechanism is on the first side of the archwire slot, and the bracket lacks any other structure inhibiting rotation of the door towards the open state on the side of the archwire slot opposite from the hinge structure.

In another aspect, the present disclosure provides a self-ligating orthodontic appliance comprising a base for bonding the appliance to a tooth surface and a body extending outwardly from the base, the body defining an archwire slot extending in a mesial-distal direction across the body. A hinge structure is disposed in the body and defines a hinge axis. A latch assembly including a door and a lock is located proximate the hinge axis. The door is rotatable about the hinge axis between an open state and a closed state, the door comprising one or more struts extending in the general direction of the base from a lingual surface of the door. The bracket further includes a first spring offset from at least a portion of the hinge structure, wherein the first spring biases the door in the direction of the archwire slot when the door is in the closed state.

In another aspect, the present disclosure provides a method of ligating a wire, the method comprising providing an orthodontic appliance comprising a base for bonding the appliance to a tooth surface and a body extending outwardly from the base and defining an archwire slot extending in a mesial-distal direction across the body. The bracket further includes a hinge structure defining a first reference axis and disposed on a first side of the archwire slot. A latch assembly is coupled to the bracket body and includes a door and a locking mechanism. The door is coupled to the hinge and rotatable about the first reference axis between an open state and a closed state, wherein an archwire is insertable into the archwire slot in the open state and the door retains the archwire in the archwire slot in the closed state. The locking mechanism engages a surface of the door and impedes rotation of the door to the open state when the door is in the closed state, wherein the locking mechanism is on the first side of the archwire slot. The method further comprises introducing an archwire into the archwire slot, disengaging the lock from the surface of the door; and rotating the door in the direction of the archwire slot to transition the door to the closed state.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

While the above-identified figures set forth several embodiments of the disclosure other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

Definitions

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF ILLUSTRATIVE EMBODIMENTS

The sections below describe illustrative embodiments directed to self-ligating orthodontic appliances and methods related thereto. These embodiments are exemplary and accordingly should not be construed to unduly limit the invention. For example, it is to be understood that one of ordinary skill can adapt the disclosed appliances and methods for attachment to either the labial or lingual surfaces of teeth, to different teeth within the same dental arch (for example, corresponding appliances on mesial and distal halves of the dental arch), or to teeth located on either the upper or lower dental arches.

The appliances and methods described herein may optionally be customized to the individual patient undergoing treatment. Material and dimensional specifications could also vary from those disclosed herein without departing from the scope of the claimed invention. Unless otherwise specified, the provided appliances and components could be constructed of any of a variety of metal, ceramic, polymeric, and composite materials known to those skilled in the art. Further, unless otherwise indicated, dimensions associated with the appliances and their components are not critical and the accompanying drawings are not necessarily drawn to scale.

Figure 1:
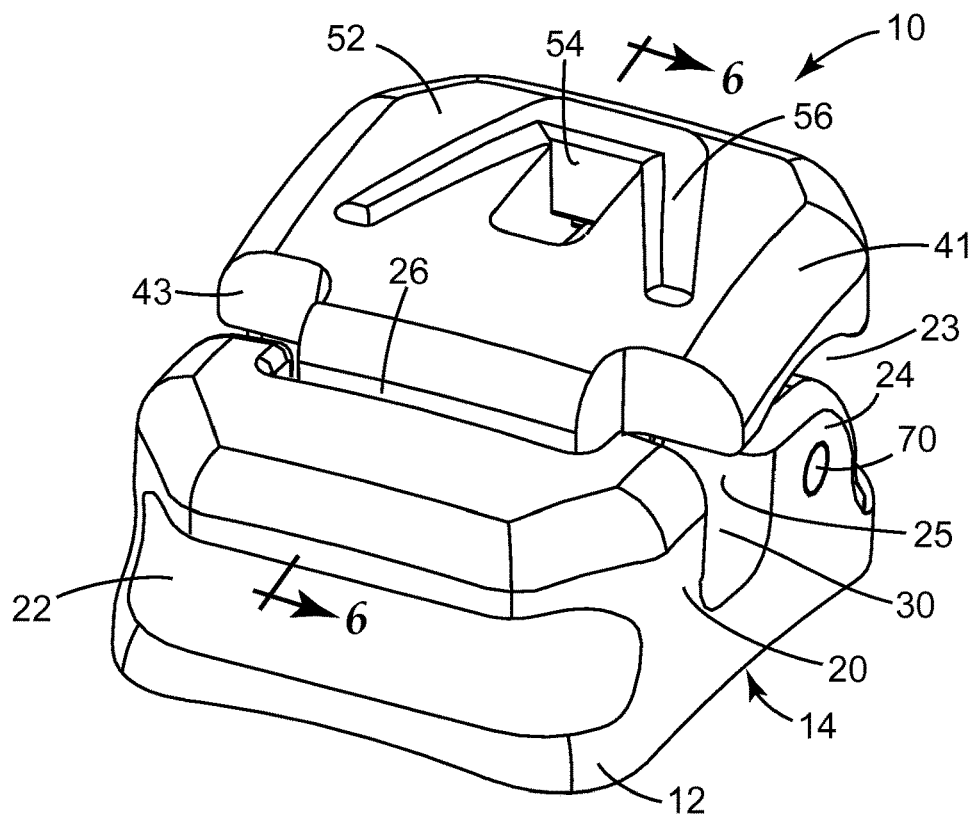
FIG. 1 is a perspective view of a self-ligating orthodontic appliance including a body and a door according to one embodiment of the present disclosure, looking towards its occlusal, facial, and mesial sides.

An orthodontic bracket 10 according to one embodiment is shown in FIGS. 1-9. Referring to FIG. 1, the appliance 10 has a base 12 having an outer surface 14 adapted for adhesive bonding to a patient's tooth. Preferably and as shown, the outer surface 14 is concave and substantially conforms to the convex outer surface of the tooth. In certain embodiments, the outer surface 14 may feature a compound contour, with curvature in both the mesial-distal and occlusal-gingival direction.

The orthodontic bracket 10 of this embodiment and the orthodontic appliances of other embodiments, unless otherwise indicated, are described herein using a reference frame attached to a labial surface of a tooth on the upper or lower jaw. Consequently, terms such as labial, lingual, mesial, distal, occlusal, and gingival used to describe the orthodontic bracket 10 are relative to the chosen reference frame. The embodiments, however, are not limited to the chosen reference frame and descriptive terms, as the orthodontic bracket 10 may be used on other teeth and in other orientations within the oral cavity. For example, the orthodontic bracket 10 may also be coupled to the lingual surface of the tooth. Those of ordinary skill in the art will recognize that the descriptive terms used herein may not directly apply when there is a change in reference frame. Nevertheless, the embodiments are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the embodiments to a particular location or orientation.

The outer surface 14 may include mesh, holes, bumps, recesses, undercuts, a microetched surface, glass grit, bonded particles, an organo-silane treated surface, or any other known mechanical or chemical modification to enhance adhesive bonding between the base 12 and the underlying tooth. Alternatively, the base 12 could also have a banded configuration in which the base 12 fully encircles the tooth to provide an even stronger bond. In other implementations, the base may include a fixed, compressible material to assist in filling gaps between the base 12 and the tooth structure. Suitable compressible materials are described in US Publication No. 2009/0233252 (Cinader).

A body 20 extends outwardly from the base 12 in a facial direction, away from the outer surface 14. Optionally and as shown, the base 12 and body 20 are integral components. In certain embodiments, the base 12 and body 20 may be integrally made, for example, via machine or mold from a polymeric material as disclosed in U.S. Pat. No. 4,536,154 (Garton, et al.), a ceramic material such as a fine-grained polycrystalline alumina as disclosed in U.S. Pat. No. 6,648,638 (Castro, et al.), or a polymer-ceramic composite such as glass-fiber reinforced polymeric composites as disclosed in U.S. Pat. No. 5,078,596 (Carberry, et al.) and U.S. Pat. No. 5,254,002 (Reher, et al.). Other suitable materials include, for example, metallic materials (such as stainless steel, titanium, and cobalt-chromium alloys) and plastic materials (such as fiber-reinforced polycarbonate).

The body 20 has a facial surface 21 and an elongated archwire slot 30 extending in a generally mesial-distal direction across the facial surface 21 of the body. Referring to the mesial view in FIG. 2, the archwire slot 30 includes a bottom, lingual wall 34 along with gingival and occlusal side walls 32, 36. The gingival wall 32 is at least partially defined by surfaces 25 of hinge support sections 24 on the gingival side of body 20 (See FIGS. 3 and 4). An archwire (not shown) is received in the archwire slot 30 and typically has a generally rectangular cross-section that substantially corresponds with walls 32, 34, 36 of the archwire slot 30. A close correspondence between the dimensions of the archwire and the archwire slot can provide for a precise coupling between the archwire and appliance 10, giving the treating practitioner a high degree of control over the movement of teeth.

In appliances of the present disclosure, other archwire geometries can be used that do not closely approximate the dimensions of the lingual and gingival walls. In certain embodiments, the side walls 32 and 36 can include a substantially equal facial-lingual height in relation to the lingual wall 34. In alternative configurations, (See FIGS. 6 and 7), a portion of the occlusal side wall 36 has a facial-lingual height 37 (in relation to the lingual wall 34) less than the height of the gingival side wall 32. Such a height disparity allows for additional rotation of a latch assembly 40 about a hinge 70 towards the lingual wall 34 of the archwire slot. The greater degree of rotation allows for a lingual surface of a door 41 to contact an archwire having smaller facial-lingual cross-sectional dimensions, providing the precise coupling between the archwire and appliance 10 typically afforded by close dimensional correspondence between the side wall height and the archwire. In other embodiments (not shown), the gingival wall 32 includes a facial-lingual height less than the facial-lingual height of the occlusal wall 36. Such constructions may allow for a thicker, potentially more robust door 41 that would otherwise interfere with the hinge support sections 24 that contribute to a taller gingival wall 32.

As shown in FIGS. 1-4 and 6-9, a hinge 70 is provided proximate hinge support sections 24 of the body 20, and at least a portion of a latch assembly 40 is rotatably coupled to the hinge 70. A door 41 of the latch assembly 40 is rotatable about the hinge 70 between open and closed orientations, so that when the door 41 is closed an archwire is held captive in the archwire slot 30. In the configuration shown in FIG. 1, the archwire would be securely ligated to the appliance 10 such that the archwire will not become accidently dislodged as a result normal chewing and brushing activity that occurs in a patient's mouth. However, the archwire can, and should typically be capable of sliding along the length of the archwire slot 30, thereby allowing the archwire to function as a track that guides the movement of maloccluded teeth. Such sliding is especially prominent as the teeth unravel during the leveling and aligning stages of treatment.

The appliance 10 has a structure that also allows for traditional methods of ligation. As shown in FIG. 1, an occlusal undercut 22 and a gingival undercut 23 are located on occlusal side and gingival side of the body 20, respectively. In the depicted embodiment, a portion of a door 41 extends beyond the gingival edge of the body 20, creating at least a portion of a tie wing and the attendant gingival undercut 23. The undercuts 22, 23 provide an area where an elastic "O"-ring ligature, powerchain, or ligature wire can be secured to retain the archwire in the archwire slot 30. Although not critical for treatment, independent ligation can be useful, for example, when closing gaps (e.g., using a powerchain) or intentionally creating friction (e.g., using elastic ligatures) during the finishing stage of treatment. Independent ligation can also, in certain circumstances, provide additional structure to impeded rotation of aspects of the latch assembly 40, particularly when received in a gingival undercut created partially by said assembly 40. In other embodiments, the appliances of the present disclosure lack undercuts or other structure enabling the attachment of elastomeric or wire ligatures.

In more detail, the latch assembly 40 includes a door 41 and a resilient lock 60, each coupled to the hinge 70. The hinge 70 in this embodiment is provided by a cylindrical hinge pin 71, operatively coupled to the door 41, the lock 60, and the body 20. The hinge pin 71 also has a longitudinal hinge axis 72 that extends along a generally mesial-distal direction, allowing relative rotation of the door 41 about the hinge axis 72 relative to the body 20 and the lock 70. Though depicted for clarity, it is not necessary that the hinge 70 comprise a hinge pin 71. Alternatively, for example, the body 20 and latch assembly 40 could be connected to each other by a flexible polymeric membrane. In another alternative, the body 20 and door 41 may each include mating curved surfaces that provide for rotation about a desire arc. As another alternative, the hinge 70 may comprise discrete mesial and distal hinge pins.

The hinge axis 72 as illustrated is located above (i.e., in a facial direction from) the lingual wall 34 of the archwire slot 30. In other embodiments, the hinge axis may be coplanar with the lingual wall 34 or below (i.e., in a lingual direction from) the lingual wall 34. Locating the hinge 70 and attendant hinge axis 72 above the lingual wall 34 may, in certain bracket configurations, allow for increased rotation of the door 41 towards the lingual wall 34 of archwire slot 30, allowing the appliance 10 to accommodate and ligate myriad archwire geometries.

Figure 3:
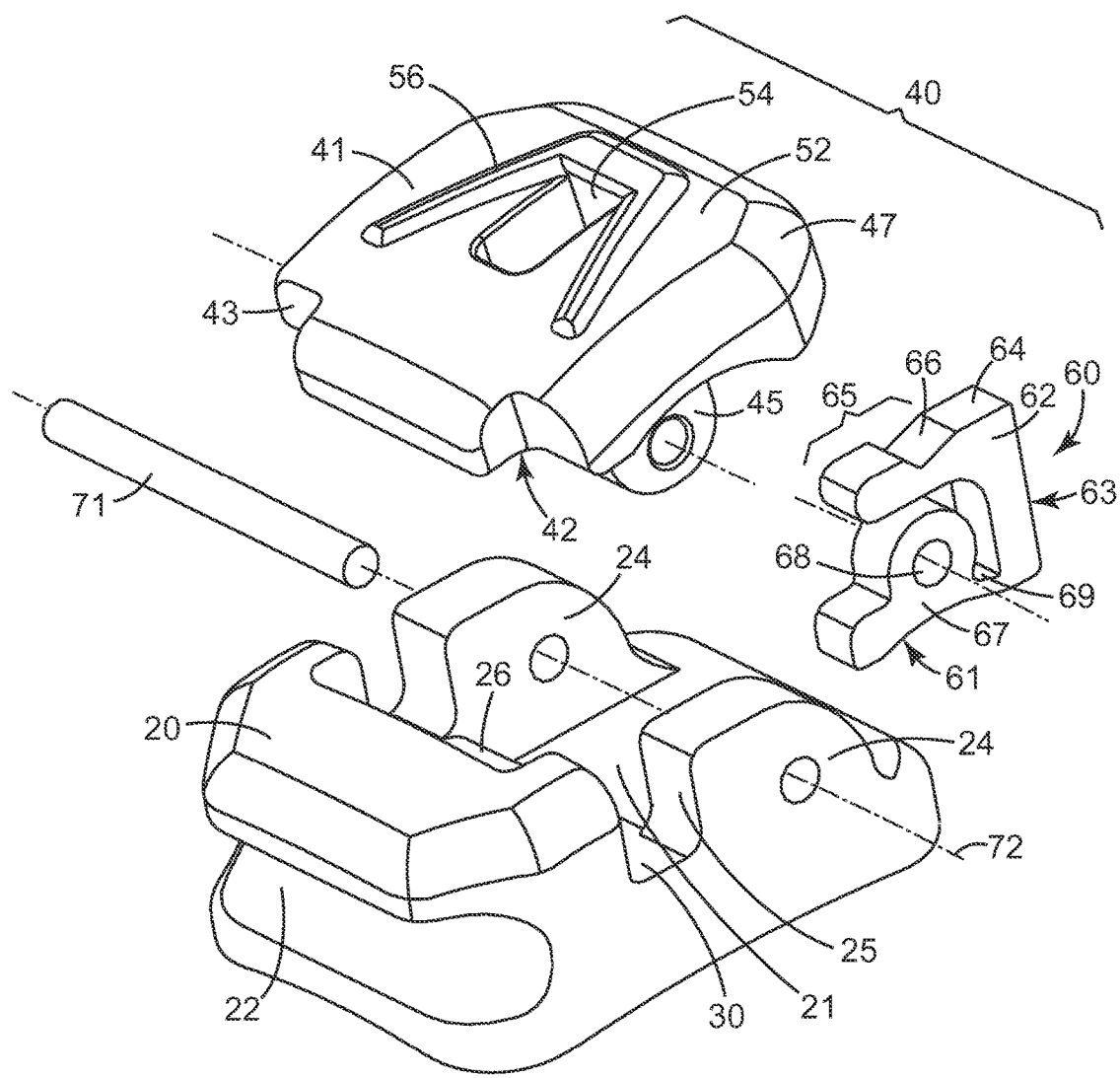
FIG. 3 is an exploded, perspective view of the appliance of FIGS. 1-2, looking toward its occlusal, facial, and mesial sides.
Figure 4:
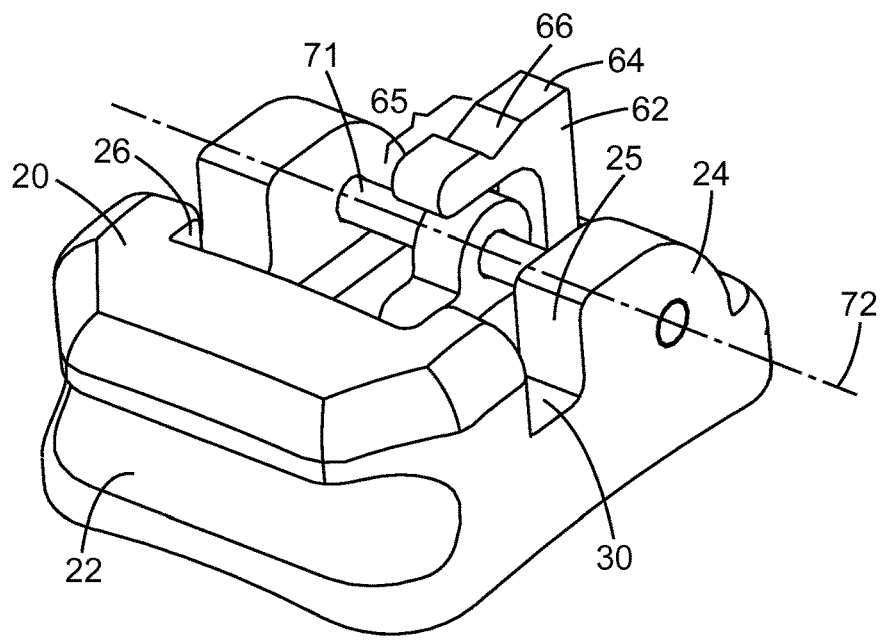
FIG. 4 is a perspective view of the appliance of FIGS. 1-3 and omitting the door, looking towards its occlusal, facial, and mesial sides.
Figure 5:
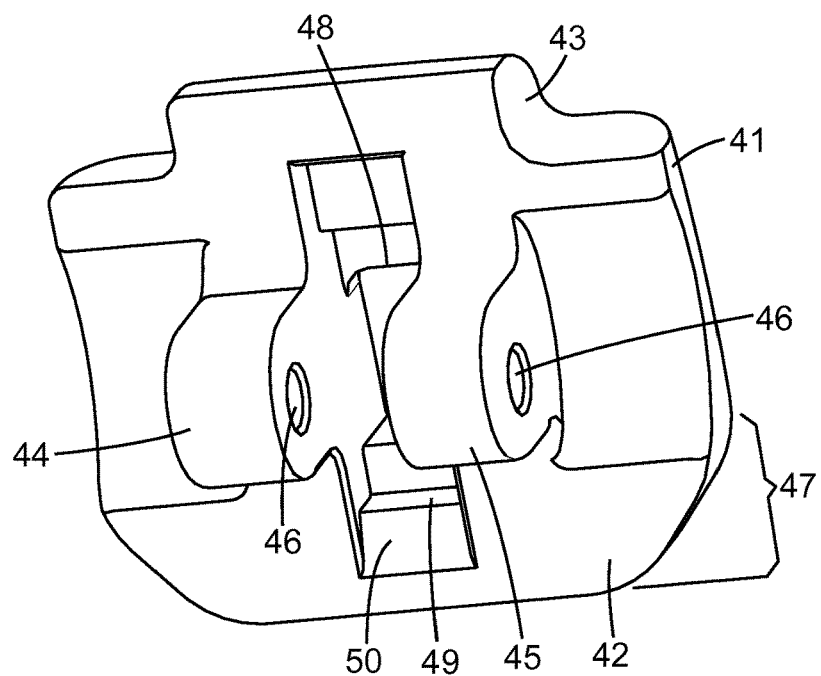
FIG. 5 is a perspective view of the ligating door of FIG. 1, looking towards its lingual side.

Referring now to FIG. 3, the lock 60 comprises a base 61 and a detent shaft 62 extending in a generally facial direction from lock base 61 and along a plane that is substantially perpendicular to the hinge axis 72. The shaft 62 includes a gingival edge 63, a facial locking surface 64, and features a facial height that is typically greater than the height of the gingival wall 32. As assembled, the shaft 62 is located in a gingival direction from hinge 70 and extends between the door 41 and the facial surface 21 of the body 20. At least a portion of the facial locking surface 64 is configured to abut a lingual surface 42 on the door 41, providing a stop against rotation in directions away from the archwire slot 30 and preventing inadvertent opening of the door 41. Moreover, the shaft 62 and locking surface 64 can also prevent inadvertent closing of the door 41 before the practitioner is prepared to begin or resume treatment. The detent shaft 62 accordingly establishes a positive locking mechanism disposed on the gingival side of both the archwire slot 30 and the hinge axis 72.

An arm 65 extends outwardly from the shaft 62 in a generally occlusal direction. The arm projects along, and is generally parallel to, the length of the base 61. In the embodiments depicted in FIGS. 1-9, the arm 65 is generally coplanar with the locking surface 64. In alternative constructions such as those depicted in FIGS. 10 and 17, the arm may extend towards the door at an obtuse angle relative to the locking surface. The arm 65 may include an indent or cut-out 66 to provide purchase for a hand instrument. Force applied to the arm 65 can create a moment about a portion of the base 61, causing the detent shaft 62 to move towards an outer end of the base 61 (e.g., eyelet 67) and disengage from the door 41. In alternative implementations, the arm 65 may be omitted or not used, with the practitioner instead applying force to the gingival edge 63 to disengage the locking surface 64 from the door 41.

The lock base 61 includes an eyelet 67 spaced from the shaft 62 in a generally occlusal direction. The eyelet 67 includes an aperture 68, allowing the hinge pin 71 to extend through the lock 60 and retain the lock 60 relative to the body 20 (See FIG. 4). In other alternative embodiments, the lock 60 may be retained by interference fit between the door 41 and body 20, potentially obviating the need for an aperture 68 for receipt of the hinge pin 71.

The lock base 61 can include a hinge section 69 having a reduced thickness disposed between the shaft 62 and the eyelet 65. The hinge section 69 enables movement to the arm 65 and the shaft 62 in directions towards the eyelet 67, with the arm 65 acting as a lever. As explained in more detail below, movement of the arm 65 in the direction of the eyelet 67 can disengage the locking surface 64 from the lingual surface 42 of door 41, allowing the door 41 to rotate relative to the archwire slot 30. The hinge section 69 may be included at least partially within the shaft 62, allowing a portion of the shaft 62 to deflect relative to the door 41 and appliance base 12.

In other embodiments (not shown), the arm 65 may extend over a facial surface of the door 41, applying a pressure in the direction of the base 12 if the door 41 is rotated away from the archwire slot 30. The lock 60 in such embodiments may function as a clip, with the practitioner rotating the arm 65 in directions away from the base 12 to allow for pivoting of the door 41 about the hinge 70.

The lock 60 is preferably made from a resilient metal alloy, such as stainless steel, titanium, cobalt-chromium alloy (such as manufactured by Elgiloy Specialty Metals, Elgin, Ill.), or a shape-memory alloy such as an alloy of nickel and titanium (e.g., Nitinol). Preferably, the lock 60 is sufficiently resilient so that the shape of the lock 60 when relaxed does not significantly change during the course of treatment. As another option, the lock 60 could be made from any other resilient material known to one skilled in the art, such as a flexible polymer or composite material. The lock 60 material should typically be resistant to inelastic deformation under compressive forces between the door 41 and the bracket body 20.

The door 41 includes a lingual surface 42 opposite a facial surface 52. The door 41 includes an occlusal edge region 43 that extends over the archwire slot 30 when the latch assembly 40 is in a closed position (See FIGS. 6 and 8). Accordingly, the lingual surface 42 beneath the occlusal edge region 43 will contact the archwire, if such contact is prescribed, when the archwire is received in the archwire slot 30. As can be appreciated by reference to FIG. 1, the occlusal edge region 43 does not extend the full mesial-distal length of the archwire slot 30 and a portion thereof is received in a recess 26 on the occlusal side of body 20. The recess 26 includes a rotation stop surface 29 disposed at the apex of the occlusal side wall 36. The rotation stop surface 29 engages the lingual surface 42 to prevent further rotation of the door 41 in the direction of the lingual wall 34.

The occlusal edge region 43 may, in certain embodiments, include at least one chamfer or other surface configuration to act as a pushing element for guiding the archwire into the archwire slot 30. Additional attributes and configurations of pushing elements may be found in U.S. Pat. No. 8,469,704 (Oda et al.).

A pair of struts 44, 45 extend outwardly from lingual surface 42 of the door 41. The struts 44, 45 are spaced apart to straddle a portion of the lock 60 when the appliance 10 is assembled, limiting mesial-distal movement of the lock 60. As assembled, the struts 44, 45 are received between hinge support sections 24 of the bracket body, aligning both the struts 44, 45 and lock 60 between the support sections 24 (See FIG. 8). Each strut includes an aperture 46, allowing the hinge pin 71 (or hinge pins) to extend through both struts 44, 45 and into hinge support sections 24 of the body 20. In other embodiments, the struts 44, 45 may include cylindrical protrusions that rotate within apertures 27 of hinge support sections 24 or within arc-shaped structures on the surface of the support sections 24. Though two struts 44, 45 are depicted, alternative bracket configurations may include a single strut adjacent a lock 60.

Figure 6:
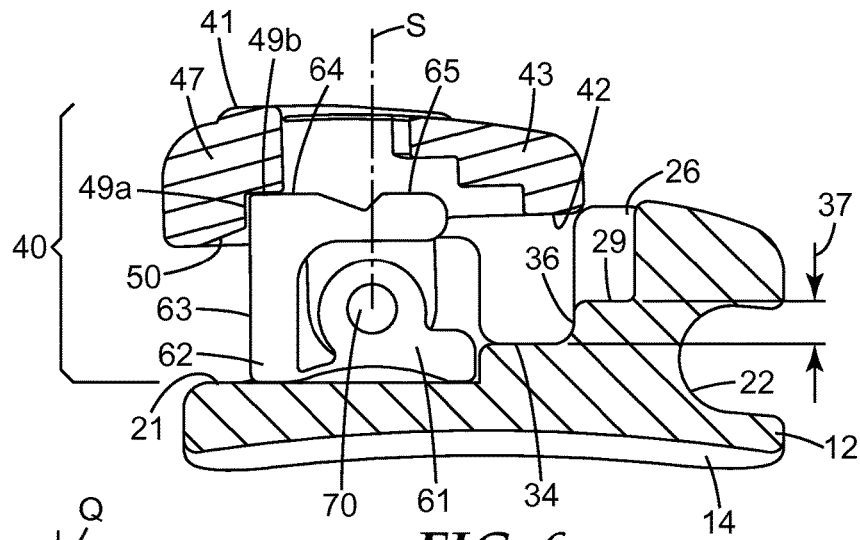
FIG. 6 is a cross-sectional view of the appliance of FIG. 1 in a closed orientation, looking toward its distal side.
Figure 7:
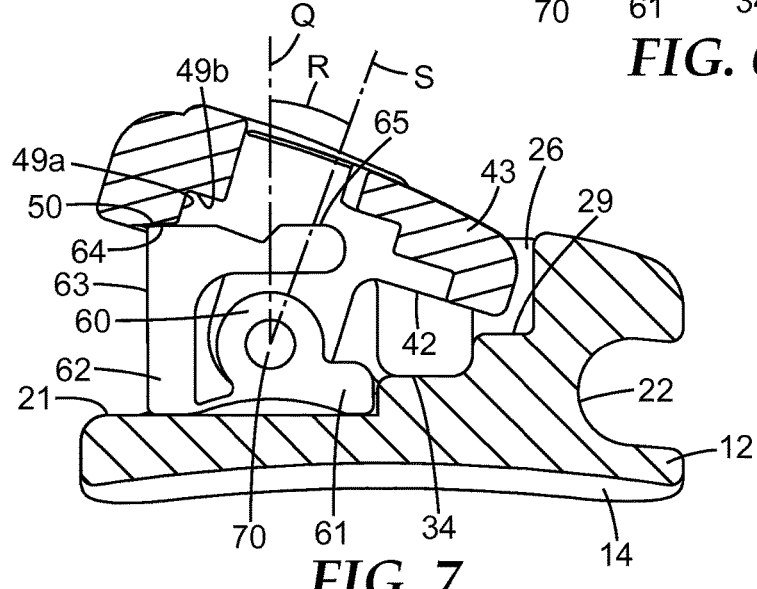
FIG. 7 is a cross-sectional view of the appliance of FIG. 1 after further rotation of the door, looking towards its distal side.
Figure 8:
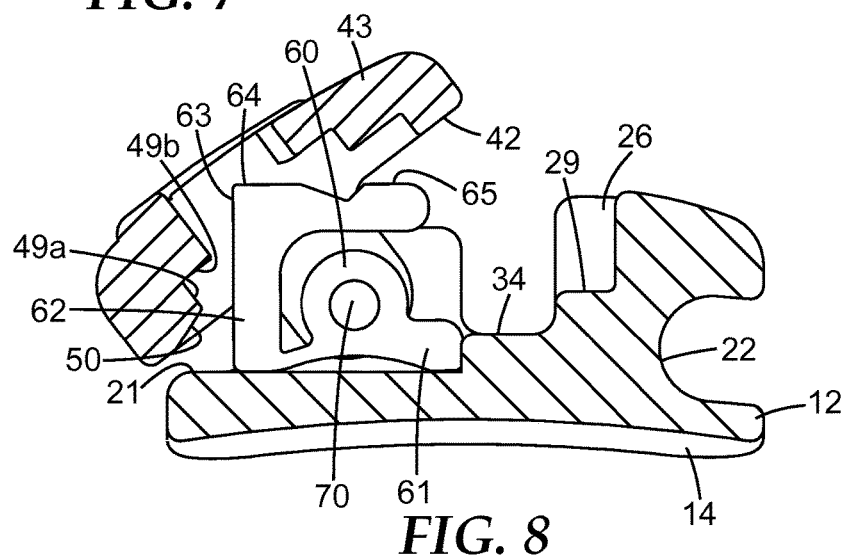
FIG. 8 is a cross-sectional view of the appliance of FIG. 2 in an open orientation, looking towards its distal side.
Figure 9:
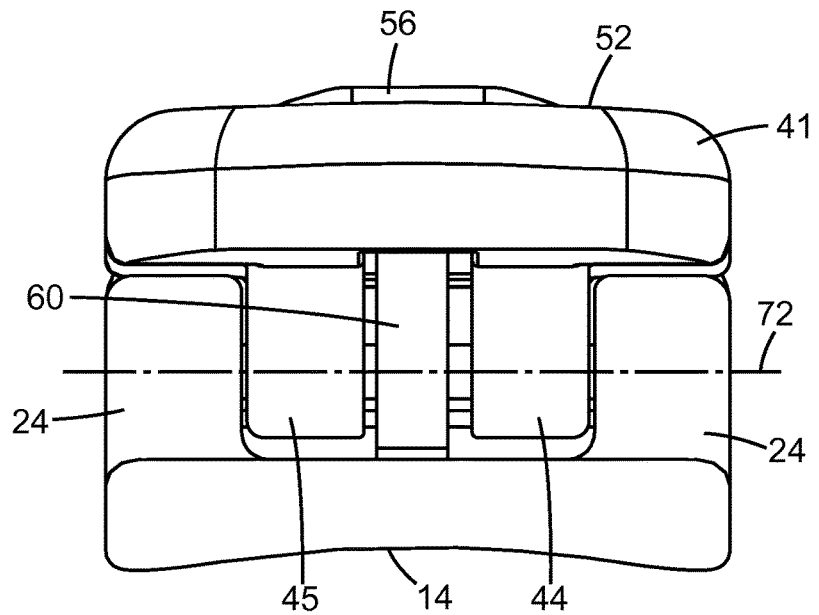
FIG. 9 is a plan view of the appliance of FIGS. 1-3, looking towards its gingival side.

The struts 44, 45 extend outwardly from a central portion of the door 41 along an axis S that is generally perpendicular to a plane tangent to the lingual surface 42, giving the door 41 a "T-shaped" appearance when viewed in the mesial direction as in FIGS. 6-8. Depending on the desired rotation of the door 41, however, the struts may protrude along an axis S extending at an oblique angle relative to the tangent plane. For example, the struts 44, 45 may protrude along an axis S that extends at an about 30 degree angle to about 150 degree angle relative to the tangent plane.

The location of struts toward the center of the lingual surface 42 creates a section 47 of the door 41 that is located in a gingival direction from the hinge axis 72 when the appliance 10 is assembled. Locating a substantial portion of the door 41 gingival to the hinge axis 72 may be advantageous in certain implementations, as the arc about which the door 41 must rotate away from the archwire slot 30 to allow entry is reduced. Furthermore, typical latch appliances are hinged at the gingival or occlusal end of the latch, creating a relatively tall appliance in the facial direction when the latch is opened. Locating the hinge axis 72 in a lingual direction from the center of the door 41 may reduce the facial height of the appliance 10 when the door 41 is opened (FIG. 8), providing a lower profile for the appliance 10 to reduce interference with adjacent oral tissue and allow treatment of otherwise crowded occlusions.

Alternative implementations, however, may include struts 44, 45 spaced closer to the occlusal or gingival edge of the lingual surface 42. Such alternative implementations of door 41 can present a generally "L-shaped" appearance when viewed in the mesial direction.

A channel 48 is defined in an area of the lingual surface 42 between struts 44, 45. The channel 48 is sized and shaped to receive the lever arm 65 of the lock 60. As depicted, the channel 48 is generally rectangular in shape at the lingual surface 42, but may be of any suitable geometry to accommodate a variety of lock 60 dimensions. In presently preferred circumstances, the channel 48 includes a variable depth relative to the lingual surface 42 along its length, allowing for one or more purchase points between the locking surface 64 and the door 41 as the channel 48 rotates relative to the lock 60. In certain implementations, the channel 48 can include a concave curvature.

The channel 48 may include one or more steps 49 including an occlusal surface 49a and a lingual surface 49b. The occlusal surface 49a may engage a gingival edge 63 of the lock 60, preventing unwanted rotation of the door 41 towards the lingual wall 34 of the archwire slot 30. In cooperation, the lingual surface 49b engages the facial surface 64 of the detent shaft 62, preventing inadvertent opening by rotation of the door 41 away from the archwire slot 30. The inclusion of multiple steps 49 in the channel 48 may allow for iterative, precise control over the position of the door 41 during treatment, as the lock 60 can engage the door 41 at several locations about the arc provided by the hinge 70. In lieu of or in addition to step(s) 49, the channel 48 may include a beveled surface 50 proximate the gingival edge of the channel 48. The beveled surface 50 extends at an angle relative to the lingual surface 42 and can engage the locking surface 64 at several locations along the arc as the door 41 is rotated towards the lingual wall 34 (FIG. 7). In alternative embodiments, the beveled surface 50 or steps 49 (or both) may be disposed directly on the lingual surface 42, and not contained within a defined channel 48.

The door 41 has a facial surface 52 that has a generally rectangular shape, similar to that of the appliance 10 as a whole when viewed from the facial direction. The facial surface 52 includes an aperture 54 that extends through the body of the door 41 to the lingual surface 42. The aperture 54 is shaped to expose at least a portion of the arm 65 and is located in a facial direction therefrom. Exposure of the lock 60 allows a practitioner to apply force to the portion of the arm 65 to effect transition of the door 41 between an open orientation (FIGS. 2 and 8) and a closed orientation (FIGS. 1 and 6). As further explained below with respect to FIGS. 6-8, application of force to the lock 60 can disengage the locking surface 64 from the lingual surface 42 or channel 48 (if present), of door 41. Disengaging the locking surface 64 allows the door 41 to rotate relative to hinge axis 72, thereby controlling access to the archwire slot 30. The facial surface 52 may also include an instrument guide 56, depicted in FIGS. 1 and 3 as a generally U-shaped trough, for guiding a hand instrument towards the aperture 54. Other configurations are possible, so long as the instrument guide 56 allows a practitioner to find purchase for a hand instrument on the facial surface 52 and advance the instrument towards the aperture 54 to disengage the lock 60.

Figure 2:
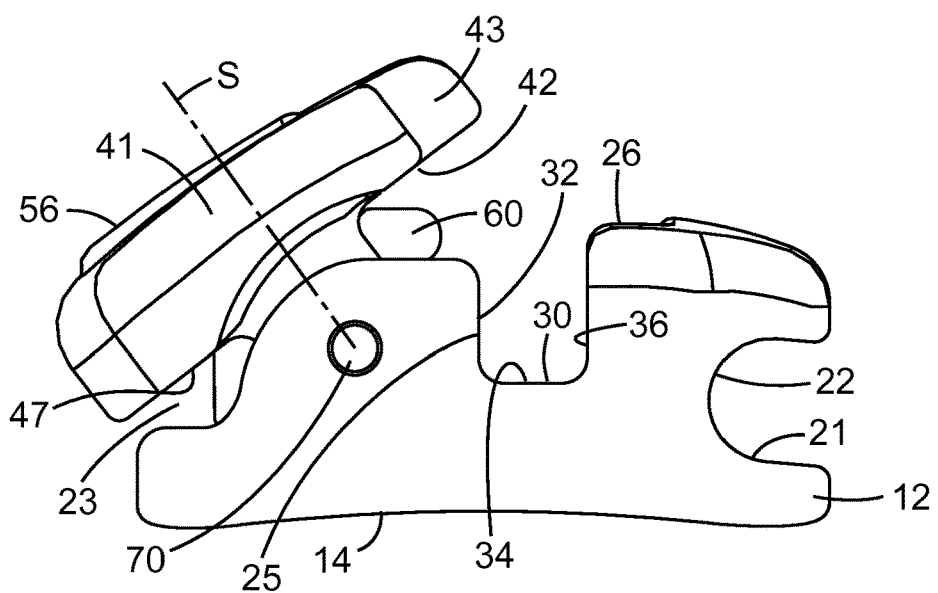
FIG. 2 is a plan view of the appliance of FIG. 1 in an opened configuration, looking toward its distal side.

The door 41 is typically machined or molded from the same materials as body 20, greatly enhancing the aesthetics of the appliance 10. The door 41 has a mesial-distal width that is at least the width of the lock 60 and hinge pin 71 between hinge support sections 24, and thus substantially obscures these ligating elements when the door 41 in its closed position. As illustrated in FIG. 2, for example, the door 41 extends over the facial surfaces of the lock 60 and hinge pin 71, causing (with the exception of portions visible through aperture 54) the lock 60 and hinge pin 71 to be obscured when viewed from the facial direction. In other implementations, the door 41 may be machined or molded from the same materials as the lock 60 and/or the hinge pin 71.

Notably, the door 41 lacks a clip or other structure for securing the latch assembly 40 to the body 20 on the occlusal side of archwire slot 30. The interaction of lock 60 with the lingual surface 42 is alone sufficient to arrest the rotation of the door 41 in the desired state. The lock 60 of the present disclosure is uniquely capable of serving at least two functions, separately or in combination. The lock 60 minimizes or prevents rotation of the occlusal edge 43 towards the archwire slot while the door 41 is in the open orientation, keeping the latch assembly from obscuring access to the archwire slot 30 as long as the locking surface 64 is engaged. This dramatically reduces the risk to the practitioner of the door 41 inadvertently closing during seating of the archwire. Similarly, the lock 60 minimizes or prevents inadvertent opening when the archwire is secured in the archwire slot 30 during treatment. The latch assembly 40 of the present disclosure accordingly grants dynamically enhanced control over access to the archwire slot 30.

By placing a positive locking mechanism on the same side of the archwire slot as the hinge axis 72, the appliance 10 is made considerably easier to open. Furthermore, the latch assembly 40 does not need to rely on a clip or other mechanism for coupling the door 41 to the body 20 on the occlusal side of the archwire slot 30 to remain closed. This grants the door 41 a smaller profile and allows for rotation of the door 41 substantially below the gingival wall 32. The greater arc of rotation provides for ligation of a greater array of archwire facial-lingual cross-sectional dimensions and provides enhanced treatment flexibility. In addition, the directionality of the hinge axis 72 can help minimize the chance of accidental door 41 opening during mastication, since the latch assembly 40 opens towards a direction away from the occlusal teeth surfaces. It should be understood, however, that the occlusal and gingival directions could easily be reversed, if desired, without affecting the operation of the appliance 10.

Beginning with the door 41 in its closed position as shown in FIG. 6, the appliance 10 can be operated by inserting the tip of a hand instrument into the aperture 54 on the facial surface 52 of door 41. The tip of the hand instrument is subsequently engaged with the arm 65, with continued force applied towards the base 12 causing the shaft 62 to rotate or otherwise move towards the archwire slot 30. This movement continues until the locking surface 64 is disengaged from the door 41. As used herein, a locking surface 64 is disengaged when surface to surface contact is lacking or otherwise insufficient to prevent rotation. With continued nudging with the hand instrument, the door 41 can be pivoted about the hinge axis 72 until it reaches the open configuration shown in FIG. 8. In this position, access to the archwire slot 30 is allowed whereby the archwire can be removed and/or replaced as the practitioner sees fit. Once the lever arm 65 is released, the detent shaft 62 will flex back into its original position between the lingual surface 41 and the facial surface 22 of the body, preventing the door 41 from pivoting closed. Subsequently, force applied to the lever arm 65 will allow the door 41 to pivot back to its closed position FIG. 6 and obstruct access to the archwire slot 30. Alternatively, the orthodontic practitioner may choose to apply pressure on the gingival edge 63 of the lock 60 proximate the locking surface 64, which can also drive the detent shaft 62 in the direction of the archwire slot 30.

The door 41 is pivotable about the hinge axis 72 towards a plurality of closed positions relative to archwire slot 30.

Optionally and as shown in FIG. 7, the occlusal edge region 43 of door 41 may be rotated beyond the closed position shown in FIG. 6. Due in part to the relative height of the occlusal wall 36, the lingual surface 42 of the edge region 43 may rotate until it is proximate to or engages rotation stop surface 29, enabling the appliance 10 to provide ligation for an archwire that includes a facial-lingual thickness less than that of the gingival wall 32. The size (including facial-lingual dimensions) of the archwire slot 30 can thus be tightly controlled, leading to improved tooth control during the finishing stages of treatment.

The appliances of the present disclosure may accordingly feature a closed state that includes numerous positions of the door 41 relative to the hinge axis 72. The plurality of closed positions of the door 41 may be identified relative to a closing arc of rotation R about the hinge axis 72 (See FIG. 7). The arc of rotation R may be characterized relative to the orientation of the reference axis S of the struts 44, 45 when at least a portion of lingual surface 42 of the occlusal edge region 43 is substantially parallel to the lingual wall 34 of the archwire slot 30 (e.g., the first closed state in FIG. 6). The orientation of axis S in the first closed state establishes a rotation reference axis Q. The arc of rotation R is accordingly defined by the orientation of strut reference axis S relative to the rotation reference axis Q in a given range of feasible door 41 positions. In some implementations, the door is pivotable in an arc R of at least 10 degrees. In some embodiments, the door is pivotable about an arc R of at least 15 degrees, in some embodiments at least 20 degrees, in some embodiments at least 25 degrees, in some embodiments at least 30 degrees, in yet other embodiments at least 45 degrees, and in yet other embodiments at least 60 degrees. A greater arc of rotation can provide improved ligation for an array of archwire dimensions, as well as provide the practitioner enhanced control and flexibility during treatment.

The lock 60 can be configured to inhibit backward rotation of the door 41 (i.e., rotation towards an open state) for each of the plurality of closed positions along the arc R that define the closed state of the appliance 10. In certain particularly advantageous implementations, interaction of the lock 60 (e.g., locking surface 64) and a door 41 surface (e.g., feature geometry in channel 48) substantially prevents the door 41 from rotating in directions away from the lingual wall 34 at any position of the door 41 along arc R. In these embodiments, the closed state of the appliance 10 effectively includes all or substantially all orientations of the door 41 along the arc of rotation R, as well as the reference orientation in FIG. 6. As used herein, backward rotation is substantially prevented if the door 41 is only capable of rotating in directions away from the lingual wall 34 about the hinge axis 72 in an arc of no greater than 5 degrees. In some implementations, the permissible arc of rotation away from the lingual wall 34 is no greater than 4 degrees, in some embodiments no greater than 3 degrees, in some embodiments, no greater than 2 degrees, in yet other embodiments no greater than 1 degree, and in yet other embodiments no greater than 0.5 degrees.

In presently preferred circumstances, the force required to open and close the latch assembly 40 is sufficiently low to enable easy operation by a practitioner but also sufficiently high such that the latch assembly 40 does not spontaneously disengage during normal patient activity that occurs during treatment, such as chewing and toothbrushing. Preferably, the threshold amount of force applied (either to lever arm 65 or an occlusal edge of the door 41) to open the latch assembly 40 is at least about 0.45 newtons (0.1 lbf), at least about 0.9 newtons (0.2 lbf), at least about 2.2 newtons (0.5 lbf), or at least about 4.4 newtons (1 lbf). The threshold force is preferably up to about 5.3 newtons (1.2 lbf), up to about 6.7 newtons (1.5 lbf), or up to about 8.9 Newtons (2 lbf).

The appliance 10 of FIGS. 1-9 is suitable for "passive ligation", in that the door 41 does not provide a continuous force on the archwire. Appliances according to the present disclosure may also be adapted for active ligation. "Active ligation" (as opposed to "passive ligation") occurs when a slotted orthodontic appliance imparts a continuous force urging the archwire toward the bottom wall (or sometimes side wall) of the slot. In later stages of treatment, when larger-sized square and rectangular archwires are typically used, "actively" seating these wires into the bracket slot can result in a more effective expression of the appliance prescription. In theory, active ligation can better transmit, for example, torque and rotational forces to the teeth. Another potential benefit of active ligation is the effect of storing some of the therapeutic force in the clip, as well as in the archwire. Some practitioners believe, in general terms, that a given wire will thus have its range of facial-lingual action increased and, therefore, produce more effective alignment than it would in a passively-ligated configuration.

Figure 10:
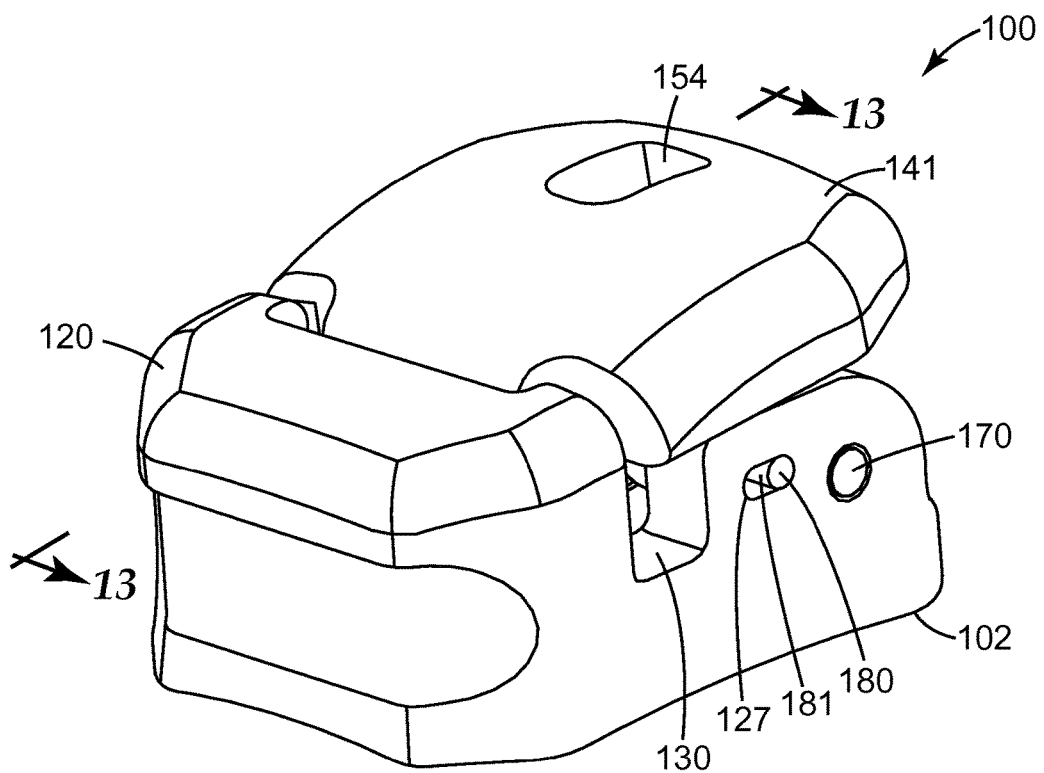
FIG. 10 is a perspective view of a self-ligating orthodontic appliance including a body and a latch assembly according to another embodiment of the present disclosure, looking towards its occlusal, facial, and mesial sides.
Figure 11:
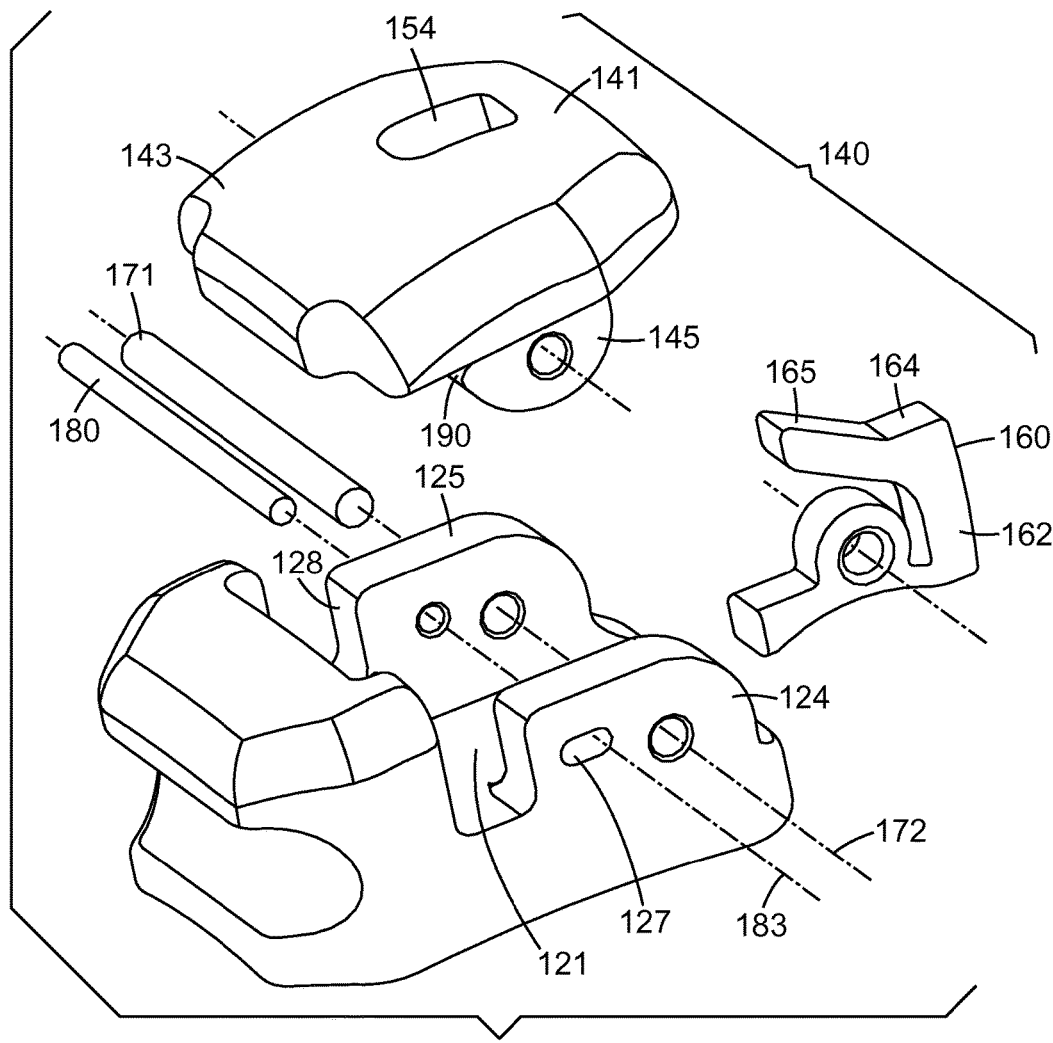
FIG. 11 is an exploded, perspective view of the appliance of FIG. 10, looking toward its occlusal, facial, and mesial sides.
Figure 12:
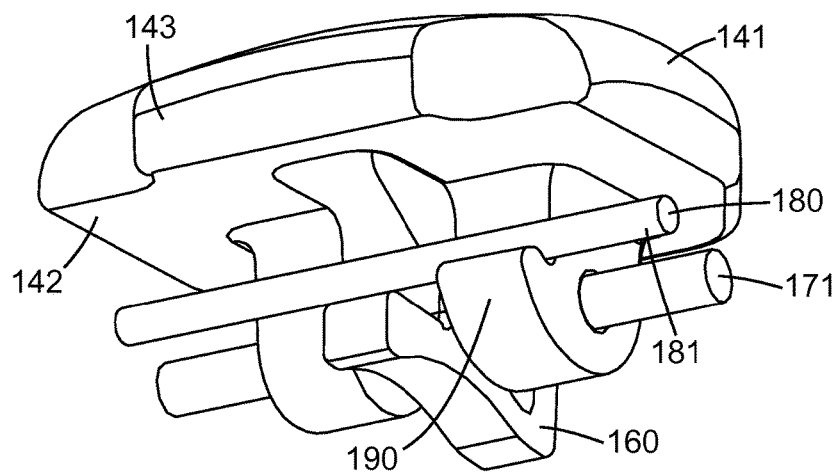
FIG. 12 is a perspective view of the latch assembly of FIGS. 10-11, looking towards the occlusal, lingual, and mesial sides.

An appliance 100 particularly adapted for active ligation is illustrated in FIGS. 10-14. The appliance 100 includes many of the same features described with respect to appliance 10. The appliance 100, however, offers added functionality and benefits as will be described below. Referring to FIG. 10, the appliance 100 has a base 102 and a body 120 similarly configured to those shown for the appliance 10 in FIGS. 1-6. Appliance 100 also has a latch assembly 140 that includes a door 141 and lock 160 aligned about a hinge axis 172 provided by hinge pin 171. Unlike appliance 10, however, the body 120 includes a spring mechanism 180 for biasing the door 141 in the direction of the lingual wall 134 of the archwire slot 130.

A deflectable spring 180 extends in a generally mesial-distal direction between mesial and distal hinge support sections 124, 125. As depicted, the spring 180 is a cylindrical beam disposed between the archwire slot 130 and the hinge 170 and is substantially parallel to the hinge axis 172. In other embodiments, however, the spring 180 may be located gingival to the hinge 170. A mesial end 181 of the spring 180 is received in a guide channel 127 in the mesial hinge support 124, while the distal end 182 is fixed in distal support section 125. The guide channel 127 allows for occlusal-gingival deflection of the spring 180 proximate the mesial end 181. As explained in further detail below in reference to FIGS. 13-14, the deflection of a portion of the spring 180 in an occlusal-gingival direction eases the transition of door 141 between open and closed orientations. In alternative implementations, the guide channel 127 may be oriented to permit facial-lingual or other directional deflection of the spring 180.

The spring 180 is typically sufficiently resilient so that the shape of the spring 180 when relaxed does not significantly change during the course of treatment. The spring 180 may be made from the same resilient materials as lock 160. In presently preferred circumstances, the spring 180 is made from a nickel-titanium alloy.

The door 141 includes one or more structures for engaging with deflectable beam 180. Turning to the latch assembly 140 illustrated in FIG. 11, the door 141 includes a strut 145 having a cam protrusion 190 extending outward from an occlusal surface thereof. The protrusion 190 features a planar surface 191 and a generally curved surface 192 joined at a deflecting ridge 193. In other implementations, the protrusion 190 can instead include two generally planar surfaces joined at a deflecting ridge, such that the protrusion present a triangular cross-section in when viewed in the mesial or distal direction. Other configurations are possible and readily apparent to those of skill in the art, provided that the protrusion 190 engages with spring 180 to bias the door 141 towards the desired position.

Figure 13:
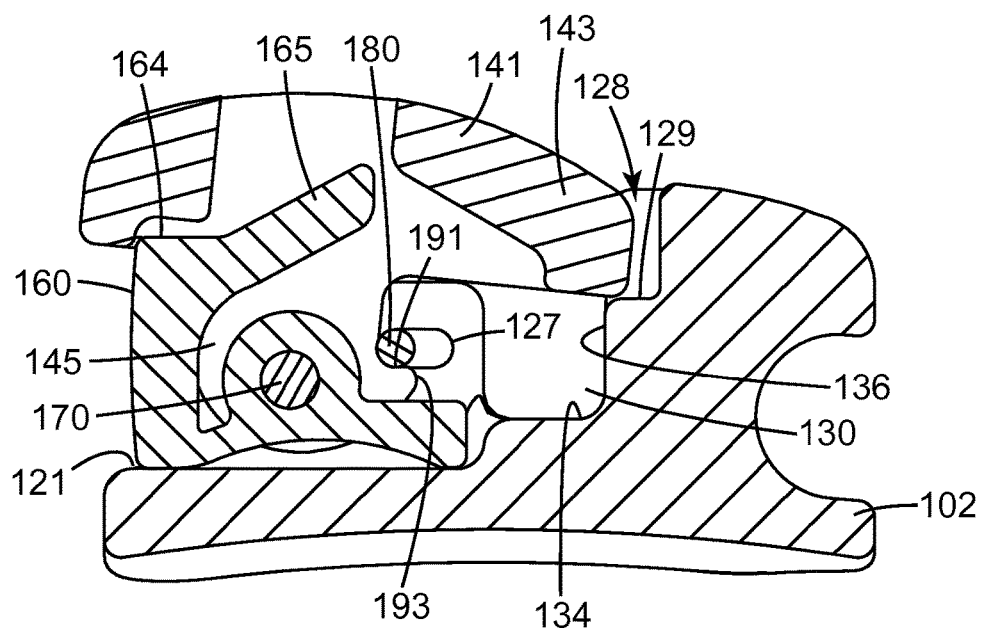
FIG. 13 is a cross-sectional view of the appliance of FIG. 10-11 in a closed configuration, looking towards its distal side.
Figure 14:
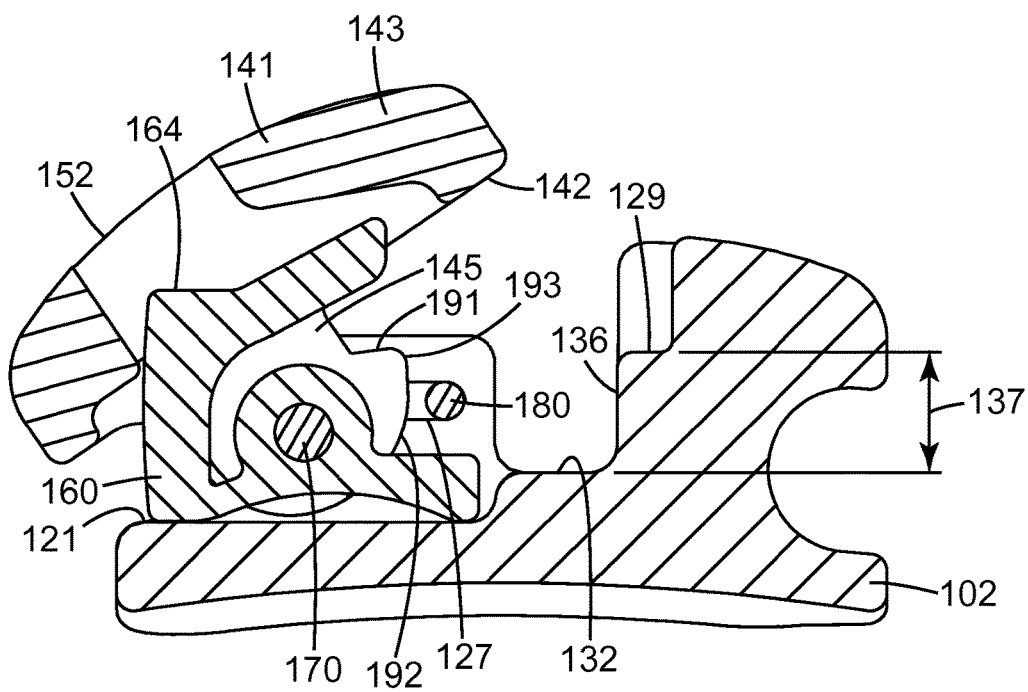
FIG. 14 is a cross-sectional view of the appliance of FIG. 10-11 in an open configuration, looking towards its distal side.
Figure 15:
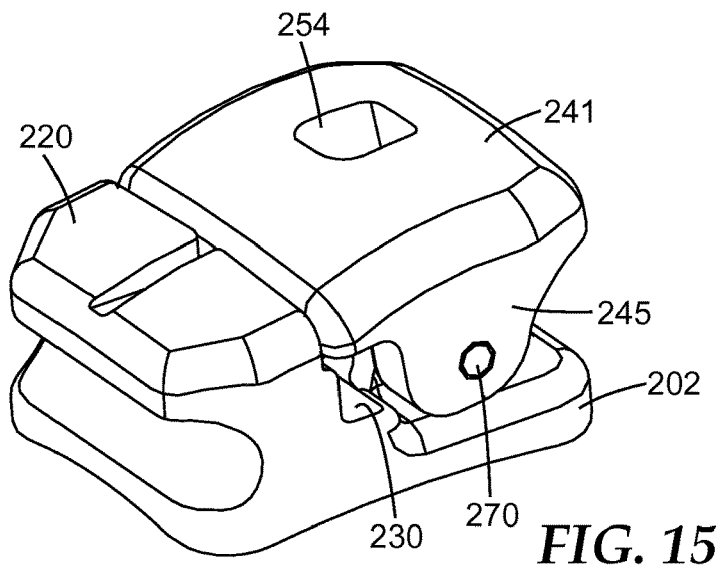
FIG. 15 is a perspective view of a self-ligating orthodontic appliance including a body and a latch assembly according to another embodiment of the present disclosure, looking towards its occlusal, facial, and mesial sides.
Figure 16:
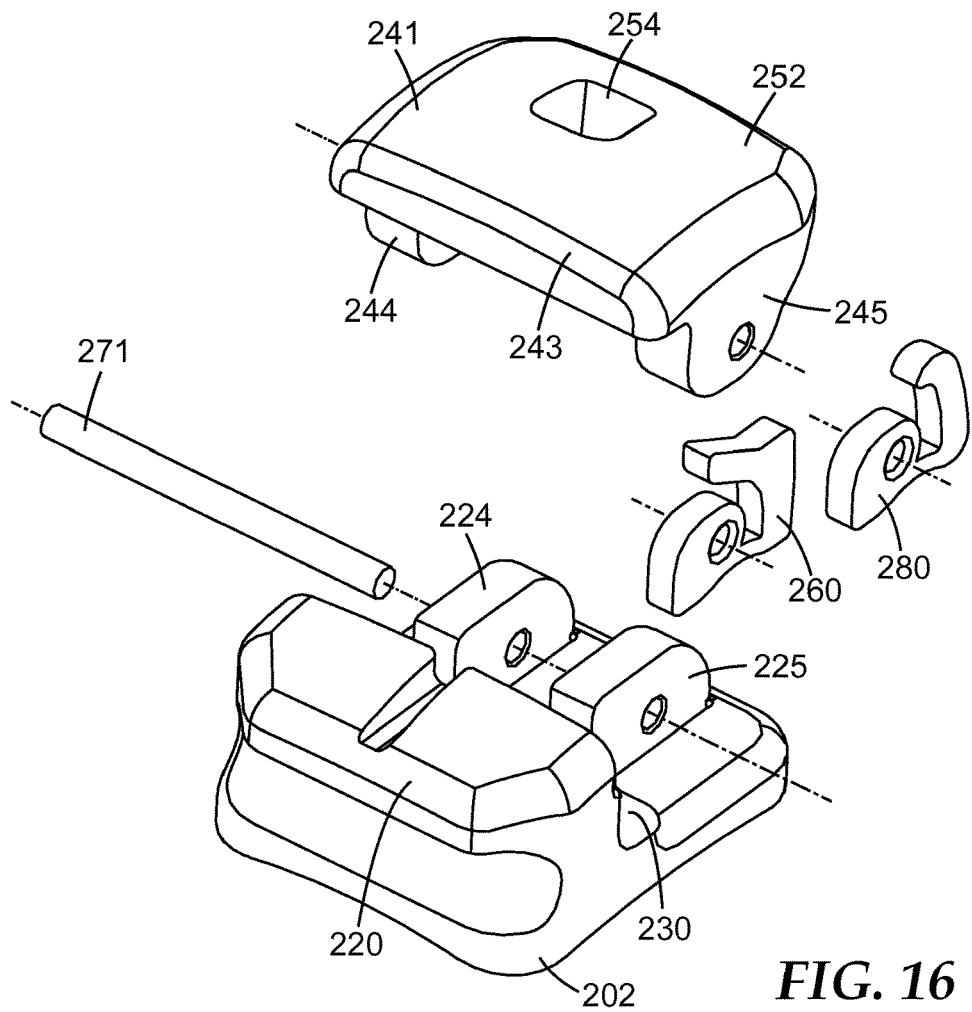
FIG. 16 is an exploded, perspective view of the appliance of FIG. 15, looking toward its occlusal, facial, and mesial sides.

The cross-sectional views of FIGS. 13 and 14, taken along the section 13-13 in FIG. 10, illustrate in greater detail the interaction between the door 141 and the spring 180. In the closed orientation shown in FIG. 13, the planar surface 191 is located between the facial surface 121 of the base 102 and the spring 180. The spring 180 exerts a downward force (in a generally lingual direction) on the planar surface 191, biasing the door 141 in the direction of the lingual wall 134 of the archwire slot 130. As a result of this downward pressure applied to the door 141, the ligation provided by the latch assembly 40 can become "active," characterized by the door 141 exerting a continuous force toward a generally lingual direction on the archwire during the course of treatment. In embodiments (not shown) featuring a spring disposed on the gingival side of a hinge axis, the spring will exert an upward force (in a generally facial direction) on a protrusion or other door engagement structure.

In presently preferred circumstances, the planar surface 191 engages the spring 180 at plurality of door 141 orientations as the door 141 pivots about the hinge axis 172. As long as there is some contact between the protrusion 190 and the spring 180, the door will be capable of applying an active force. As depicted, the planar surface 191 extends for an occlusal-gingival length at an obtuse angle relative to the occlusal strut surface 194. Factors at least partially dictating number of orientations where the engagement between the protrusion 190 and the spring 180 is feasible include: 1) the orientation of the planar surface 191 relative to the occlusal surface 194 of the strut 45; 2) the occlusal-gingival length of the planar surface 191; and 3) the height of the spring 180 relative to the facial surface 121. In alternative embodiments, the protrusion 190 may feature a plurality of steps, similar to channel 48 of door 41, such that the protrusion 190 resembles a gear shaft in mesial-distal directions. The steps provide multiple points of engagement for the spring 180 as the strut 145 is pivoted about the hinge axis 172, allowing the appliance 100 to provide more precise active ligation for an enhanced range of archwire geometries.

A portion of the occlusal edge region 143 of door 141 is received within a generally rectangular recess 128 on the occlusal side of the body 120. The recess 128 includes a rotation stop surface 129 disposed at the apex of a certain mesial-distal length of the occlusal side wall 136; as illustrated, the rotation stop surface 129 does not extend the full mesial-distal length of the archwire slot 130, but other configurations will be understood by one skilled in the art to be within the scope of disclosure. The rotation stop surface 129 engages the lingual surface 142 prevent further rotation of the door 141 in the direction of the lingual wall 134. The facial-lingual height 137 of the occlusal side wall 136 along the recess 128 thus determines, in part, the range of archwire motion and/or size dimensions over which the active ligation is possible. The facial-lingual dimension of the archwire slot (with the latch assembly 140 in its closed position) can accordingly be designed to enable active ligation when an archwire exceeds a certain facial-lingual thickness. As long as the selected archwire has a facial lingual thickness greater than or equal to the height 137 of the rotation stop surface 129, the door 141 can provide a continuous force on the archwire during the course of treatment. An archwire having a facial-lingual thickness less than height 137 of the occlusal side wall 136 may not consistently undergo active ligation so long as the archwire remains seated on the lingual wall 134.

In addition to the potential benefits of active ligation, the deflectable spring 180 provides additional insurance, in cooperation with the lock 160, against unwanted opening or closing of door 141. When the door 141 is closed over the archwire slot 130 as shown in FIG. 13, the spring 180 provides a bias on the planar surface 191 of the protrusion 190 in the direction the base 102, thereby inhibiting the door 141 from rotating in the opposite direction. When the door 141 is in the open state of FIG. 14, the spring 180 engages the curved surface 192 to prevent the door 141 from pivoting closed. The deflectable nature of spring 180 and cooperating features on the door 141 still permit rotation if deliberate force is applied by the practitioner. As sufficient force is applied to rotate the door 141 by a hand instrument, for example, the deflecting ridge 193 of the protrusion 190 will deflect the mesial end 181 of the spring 180 within the guide channel 127. This deflection allows for continued rotation of the door 141 and the protrusion 190 to the desired orientation.

Another potential advantage of the appliance 100 is an increased mesial-distal length along which the archwire can contact the lingual surface 142 of door 141. Unlike the occlusal edge region 43 of appliance 10, the occlusal region 143 of the door 141 spans the entire mesial-distal length of the archwire slot 130. Because the door 141 can engage the archwire at two locations that are spaced apart from each other along a mesial-distal direction, it is possible to reduce angular slop in the archwire and achieve greater rotation control than otherwise achievable by engaging the archwire at a single location. As can be appreciated by one skilled in the art, the mesial-distal width of occlusal edge region 143 of the door 141 may be extended to similarly span the length of an archwire slot.

FIGS. 15-21 illustrate an appliance 200 according to still another embodiment of the present disclosure. The appliance 200 has many of the same features as the appliances 10 and 100, including a base 202, body 220 with an archwire slot 230, and latch assembly 240 including a door 241 and a lock 260. Unlike appliance 100, however, the latch assembly 200 includes a spring mechanism 280 extending in a facial-lingual direction and at least partially aligned with the lock 260 along the hinge 270. In addition, the door 241 features struts 244, 245 that straddle the hinge support sections 224, 225 of the body 220. Moreover, the aperture 254 on the facial surface 252 of the door 241 is slightly offset from the central, occlusal-gingival axis 258 (See FIG. 19) in order to accommodate the inclusion of a spring 280 aligned with and directly adjacent the lock 260.

Figure 17:
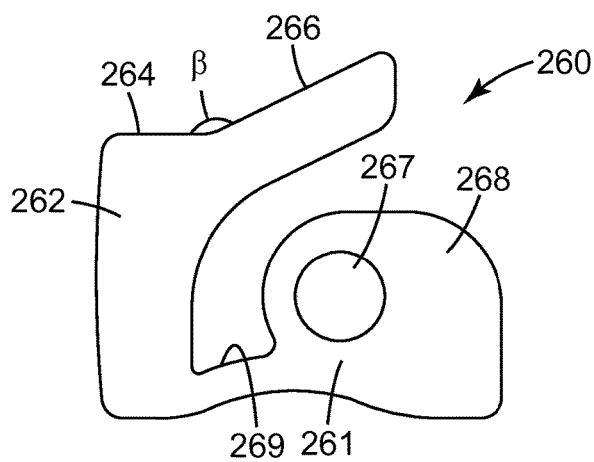
FIG. 17 is a plan view of a lock useful in the latch assembly of the appliance of FIGS. 15-16, looking at its distal side.

As illustrated in FIG. 17, the lock 260 is similar to locks 60 and 160, and features: a base 261; a detent shaft 262; a locking, facial surface 264; a deflectable arm 265; an eyelet 266; and an aperture 267 for receipt of a hinge pin 271. The lock 260 features an arm 265 that extends in an occlusal-facial direction at an obtuse angle "B" relative to the locking surface 264. This configuration can place the operative portion of the arm 265 closer to the aperture 254 on the door 241, reducing the travel necessary for a hand instrument or other implement to disengage the lock 260 from the lingual surface 242. The eyelet 266 also features an enlarged area 268 in the occlusal direction of the aperture 267, providing an occlusal surface having a greater height relative to the detent shaft 262 than locks 60 and 160.

Figure 18:
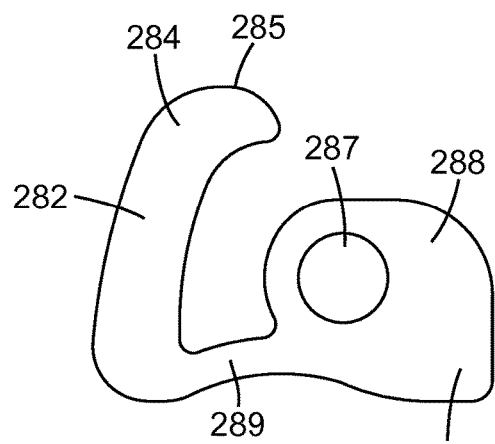
FIG. 18 is a plan view of a spring useful in the latch assembly of the appliance of FIGS. 15-16, looking at its distal side.
Figure 19:
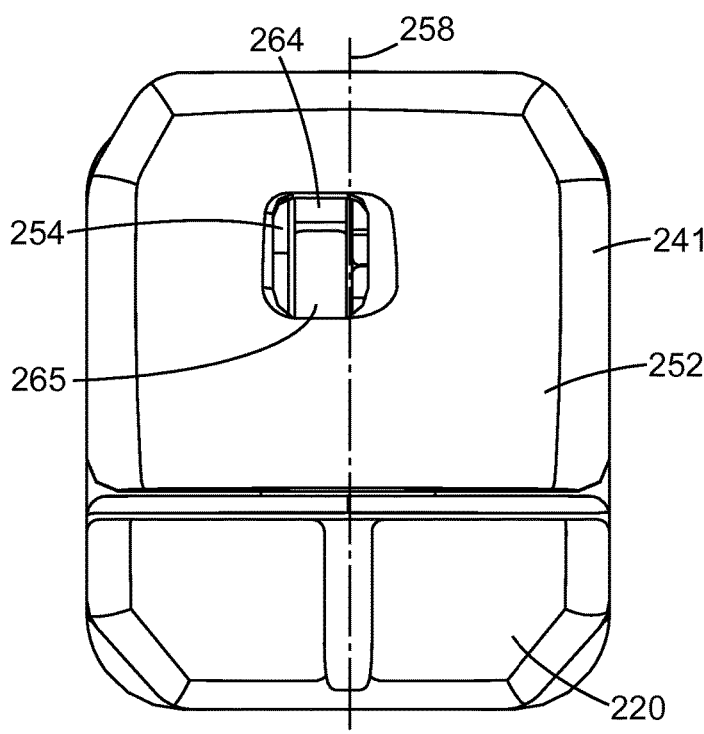
FIG. 19 is a plan view of the appliance of FIGS. 15-16 and 18, looking at its facial surface.

Referring to FIG. 18, the spring 280 has a similar construction to lock 260. The spring 280 includes a base 281 and an eyelet 286 having an aperture 287 and an enlarged area 268 in the occlusal direction of the aperture 287. A biasing shaft 282 extends in a facial direction from the base 281, terminating in a curved head portion 284. The head portion 284 is tapered over a designed radius to engage a cooperating lingual surface of a door 241. The spring 280 may optionally include a hinge section 289 having a reduced thickness relative to the remaining portion of the base 281. The hinge section 289 may allow biasing shaft 282 to deflect towards the archwire slot 230 and away from the lingual surface 242 of the door 241 when sufficient rotational force is applied to the door 241. Also, like lock 260, spring 280 features an enlarged area 288 in the occlusal direction of the aperture 287.

Figure 20:
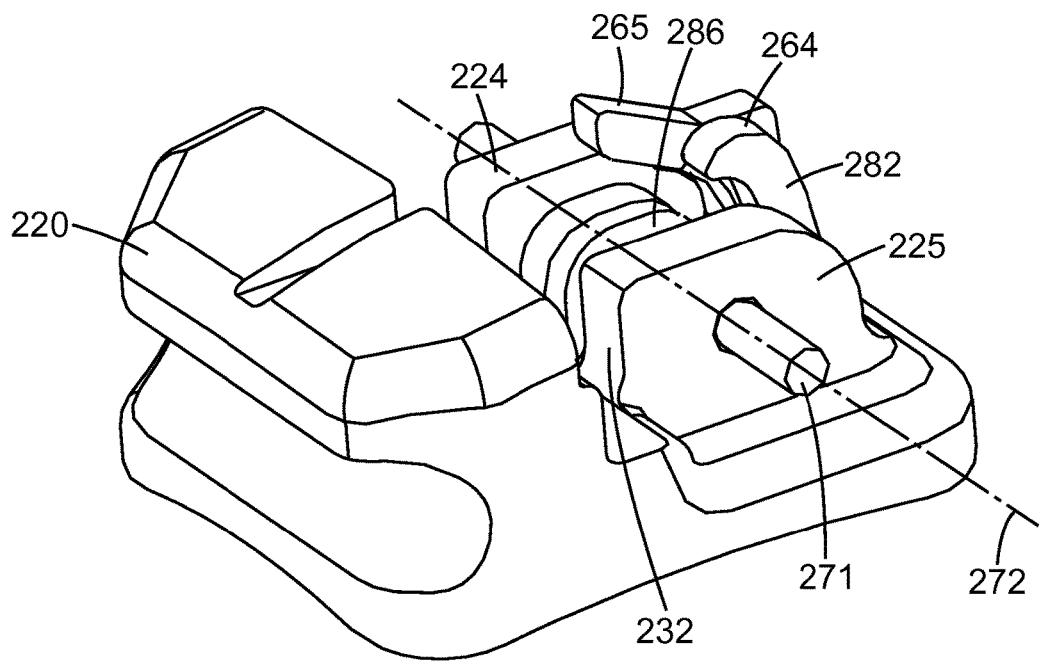
FIG. 20 is a perspective view of the appliance of FIGS. 15-16 and omitting the door, looking towards its occlusal, facial, and mesial sides.

Turning to FIG. 20, the lock 260 and spring 280 are received on the body 220 between hinge support sections 224, 225 and are aligned along hinge axis 272. In contrast to the deflectable beam of spring 180, the biasing shaft 282 extends along an axis that is decidedly not parallel to the hinge axis. The biasing shaft 282 may extend along an axis that is generally orthogonal to the hinge axis, or one that is obliquely angled relative thereto. Occlusal surfaces of lock 260 and spring 280 define a portion of the gingival wall 232 of the archwire slot 230, along with occlusal surfaces of hinge support sections 224, 225. The occlusal surfaces of lock 260 and spring 280 need not be coplanar with each other and/or the occlusal surfaces of hinge support section 224, 225. Both the locking surface 264 and the curved head portion 284 reside above the facial surface 226 of the support sections 224, 225. The biasing shaft 282 features a greater facial height than detent shaft 262, causing the curved head portion 284 to extend beyond the locking surface 264. The difference in height between the detent shaft 262 and the biasing shaft 282 allows the spring 280 and the lock 260 to operate against different surface topography on the lingual surface 242 of the door 241. The angled arm 265 extends to a greater height relative to the base 12, however, than curved head portion 284. In other implementations of the present disclosure, the locking surface 264 can extend to a greater or equal facial height in relation to the curved head portion 284.

Figure 21:
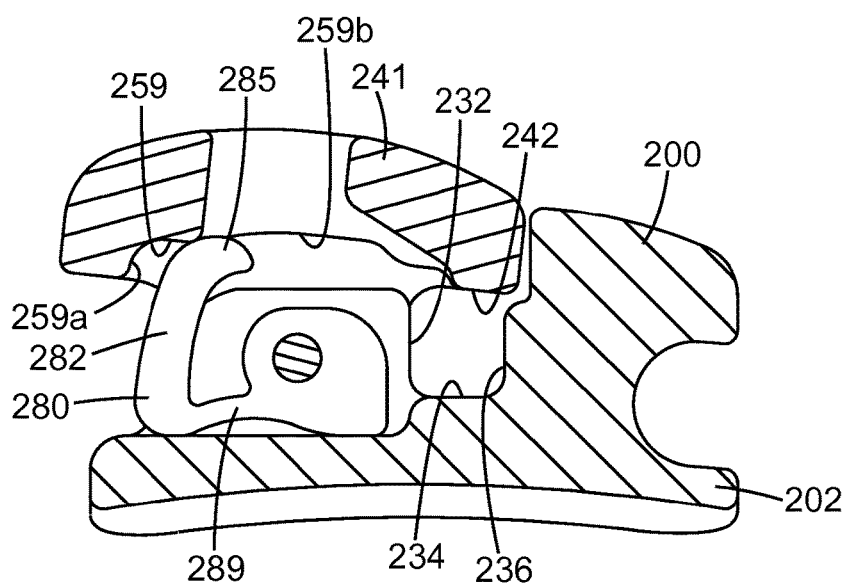
FIG. 21 is a cross-sectional view of the appliance of FIG. 15 in a closed configuration, looking towards its distal side.

When the door is closed as in FIG. 21, the apex 285 of the head portion 284 engages a region 259 of the lingual surface 242 of the door 241. In contrast to the downward pressure provided by spring 180, the spring 280 exerts an upward (i.e., in a generally facial direction) force on the gingival region of the door 241, biasing the door 241 in the direction of the archwire slot 230. The engaging region 259 of the door 241 may be contained within a channel along with other locking features (e.g., beveled surfaces or steps) or may define a portion of the lingual surface 242.

In presently preferred circumstances, the engaging region 259 includes a surface curvature to correspond to the tapering radius of head portion 284. Advantageously, the surface curvature on the lingual surface 242 can assist in deflecting the biasing shaft 282 towards the archwire slot 230 as the door 241 is rotated to the open position. Deflecting the biasing shaft 282 towards the archwire slot 230 prevents the spring 280 from inhibiting transition of the door between the closed state and the open state. In other implementations, the complimentary curves of engaging region 259 and head portion 284 do not necessarily result in the deflection of biasing shaft 282, but cooperate to reduce the likelihood of the spring 280 jamming the rotation of the door and preserve a consistent force need to open the door 241.

In certain potentially advantageous embodiments, as depicted in FIG. 21, the engaging region 259 may include compound curvature in the occlusal-gingival direction. A first surface portion 259a including a first curvature engages the head portion 284 when the door is in a closed state and is located proximate the gingival region of the door 241. A second surface portion 259b including a second curvature extends from an edge of the first surface portion 259a to at least the leading, occlusal edge region 243 and engages (continuously or periodically) or allows unrestricted travel of the head portion 284 as the door transitioned to an open state. The first curvature is typically less than the second curvature, as this ensures the desired engagement and upward pressure when the door 241 is rotated closed, while preventing the head portion 284 from contributing to binding friction or otherwise inhibiting desired rotation as the door is opened.

It is to be understood that many aspects of the appliances 100, 200 are analogous to those of the appliance 10 as previously described. Accordingly, corresponding options and features of the appliances 100, 200 need not be repeated.

Embodiments

1. A self-ligating orthodontic appliance comprising, a base for bonding the appliance to a tooth surface; a body extending outwardly from the base, the body defining an archwire slot extending in a mesial-distal direction across the body; a hinge structure defining a first reference axis, the structure disposed on a first side of the archwire slot; a door coupled to the hinge and rotatable about the first reference axis between an open state and a closed state, the door including a lingual surface and connected to the hinge structure, wherein an archwire is insertable into the archwire slot in the open state and the door retains the archwire in the archwire slot in the closed state; and a locking mechanism engaging the door, impeding rotation of the door to the open state when the door is in the closed state, wherein the locking mechanism is on the first side of the archwire slot, and wherein the bracket lacks any other structure inhibiting rotation of the door towards the open state on the side of the archwire slot opposite the hinge structure.

2. The bracket of embodiment 1, wherein the locking mechanism comprises a shaft extending in a facial direction relative to the base and engaging a lingual surface of the door.

3. The bracket of embodiment 2, wherein, when the shaft is engaged with the lingual surface, attempted rotation of the bracket towards the open state compresses the shaft, preventing further rotation towards the open state.

4. The bracket of embodiment 2, wherein the locking mechanism includes a lever arm extending in a generally occlusal-gingival direction from a portion of the shaft, the lever arm deflectable in the direction of the base to disengage the shaft from the door.

5. The bracket of embodiment 4, wherein the door includes a channel in a lingual surface, and wherein the lever arm is received in the channel.

6. The bracket of embodiment 5, wherein the door includes a labial surface and an opening extending from the labial surface to the lingual surface, wherein the opening is disposed proximate the channel allowing access to the lever arm.

7. The bracket of embodiment 6, wherein the lever arm is deflectable in a direction towards the base of the bracket, and wherein the deflection of the lever towards the base rotates the shaft in a direction away from the lingual surface of the door.

8. The bracket of any of the previous embodiments, wherein the lingual surface of the door includes a recessed area including a concave surface.

9. The bracket of embodiment 8, wherein the shaft includes a stop at an apex of the shaft, and wherein the stop is received in the recessed area of the lingual surface.

10. The bracket of embodiment 9, wherein the stop is configured to engage the concave surface of the door, whereby the door is biased in a direction towards the base and inhibited from further rotation at any selected degree of angular rotation about the first reference axis.

11. The bracket of any of the previous embodiments, wherein the hinge structure is disposed between the shaft and the archwire slot.

12. The bracket of any of the previous embodiments, wherein the reference axis is located in a generally occlusal direction from at least a portion of the door.

13. The bracket of any of the previous embodiments, wherein a portion of the lingual surface of the door is located in a gingival direction from the hinge structure.

14. The self-ligating bracket of any of the previous embodiments, wherein the door includes one or more struts extending from the lingual surface along a second reference axis.

15. The self-ligating bracket of any of the previous embodiments and further comprising a deflectable spring extending along at least a portion of the first reference axis.

16. The bracket of embodiment 15, wherein the door includes a strut extending from the lingual surface along a second reference axis that is substantially perpendicular to the spring when the door is in the closed state.

17. The bracket of embodiment 15, wherein the door includes a strut extending from the lingual surface of the door and including a protrusion abutting the spring, and wherein the spring engages the protrusion to bias the door in the general direction of the base when the door is in the closed state and engages the protrusion to bias the door in the direction away from the base when the door is in the open state.

18. The bracket of any of the previous embodiments, wherein the door includes a first strut and a second strut, and wherein a portion of the locking mechanism is disposed between the first and second legs.

19. The bracket of any of the previous embodiments, wherein the archwire slot is partially defined by a gingival wall portion and an occlusal wall portion, the bracket including a first facial surface at the apex of the occlusal wall portion and a second facial surface at the apex of the gingival wall portion, and wherein a lingual surface of the door contacts the first facial surface when the door is in the closed state.

20. The bracket of embodiment 19, wherein the gingival wall portion includes a height that is greater than a height of the occlusal wall portion, such that the first facial surface is located closer to the base than the second facial surface.

21. The bracket of embodiment 15, wherein the hinge structure and spring extend along axes that are generally parallel to the archwire slot.

22. The bracket of any of the previous embodiments, wherein the locking mechanism biases the door towards the base in the closed state.

23. The bracket of any of the previous embodiments, wherein the locking mechanism inhibits rotation of the door away from the archwire slot in the closed state and inhibits rotation of the door towards the archwire in the open state.

24. A self-ligating orthodontic appliance comprising, a base for bonding the appliance to a tooth surface; a body extending outwardly from the base, the body defining an archwire slot extending in a mesial-distal direction across the body; a hinge structure defining a first reference axis; a door rotatable about the first reference axis between an open state and a closed state, the door comprising one or more struts extending in the general direction of the base from a lingual surface of the door; and a first spring offset from at least a portion of the hinge structure, wherein the first spring biases the door in the direction of the archwire slot when the door is in the closed state.

25. The bracket of embodiment 24, wherein the spring comprises a deflectable beam extending along a second reference axis that is substantially parallel to the first reference axis.

26. The bracket of embodiment 25, wherein the door includes a protrusion abutting the beam, and wherein the beam engages the protrusion to bias the door in the general direction of the base when the door is in the closed state and engages the protrusion to bias the door in the direction away from the base when the door is in the open state.

27. The bracket of embodiment 25, wherein opening the door causes a portion of the protrusion to move in a direction away from the base, whereby the beam is deflected.

28. The bracket of any of the previous embodiments, a further including a locking mechanism engaging a surface of the door, biasing the door towards the base in the closed state to impede rotation of the door to the open state, wherein the locking mechanism is on the first side of the archwire slot.

29. The bracket of embodiment 28, wherein the bracket lacks any other structure inhibiting rotation of the door towards the open state on the side of the archwire slot opposite the hinge structure.

30. The bracket of embodiments 28 or 29, wherein, when the spring is engaged with the lingual surface, attempted rotation of the bracket towards the open state compresses the beam, preventing further rotation towards the open state.

31. The bracket of embodiment 30, wherein the locking mechanism comprises a shaft extending in a generally facial direction relative to the base and a lever arm extending in a generally mesial-distal direction, the lever arm deflectable in the direction of the base to disengage the shaft from the door.

32. The bracket of embodiment 31, wherein the door includes a channel in a lingual surface thereof, and wherein the lever arm is received in the channel.

33. The bracket of embodiments 31 or 32, wherein the lever arm is deflectable in a direction towards the base of the bracket, and wherein the deflection of the lever towards the base rotates the beam in a direction towards the archwire slot.

34. The bracket of any of the previous embodiments, wherein the lingual surface of the door includes a recessed area including a concave surface.

35. The bracket of embodiment 34, wherein the strut includes a stop extending in a facial direction above the lever arm, and wherein the stop is received in the recessed area of the lingual surface.

36. The bracket of embodiment 35, wherein the stop is configured to engage the concave surface of the door, whereby the door is biased in a direction towards the base and inhibited from further rotation at any selected degree of angular rotation about the first reference axis.

37. The bracket of any of the previous embodiments, wherein the reference axis is located in a generally occlusal direction from at least a portion of the door.

38. The bracket of any of the previous embodiments, wherein a portion of the lingual surface of the door is located in a gingival direction from the hinge structure.

39. The bracket of any of the previous embodiments, wherein the archwire slot is partially defined by a gingival wall portion and an occlusal wall portion, the bracket including a first facial surface at the apex of the occlusal wall portion and a second facial surface at the apex of the gingival wall portion, and wherein a lingual surface of the door contacts the first facial surface when the door is in the closed state.

40. The bracket of embodiment 39, wherein the gingival wall portion includes a height that is greater than a height of the occlusal wall portion, such that the first facial surface is located closer to the base than the second facial surface.

41. The bracket of any of the previous embodiments, wherein the hinge structure and spring extend along axes that are generally parallel to the archwire slot.

42. The bracket of any of embodiments 24-40, wherein the spring extends within a plane that is substantially orthogonal to the hinge axis.

43. A method for ligating an archwire, the method comprising: providing an orthodontic appliance of any of the previous embodiments; introducing a archwire into the archwire slot; disengaging a lock from the surface of the door; and rotating the door in the direction of the archwire slot to transition the door to the closed state.

44. A self-ligating orthodontic appliance comprising, a base for bonding the appliance to a tooth surface; a body extending outwardly from the base, the body defining an archwire slot extending in a mesial-distal direction across the body and including a lingual wall; a hinge structure defining a first reference axis, the structure disposed on a first side of the archwire slot; a door coupled to the hinge and rotatable about the first reference axis between an open state and a closed state, the door including a lingual surface and connected to the hinge structure, wherein an archwire is insertable into the archwire slot in the open state and the door retains the archwire in the archwire slot in the closed state; and a locking mechanism engaging the door and disposed on the first side of the archwire slot, impeding rotation of the door to the open state when the door is in the closed state, wherein the closed state comprises a plurality of door positions relative to the lingual wall, and wherein the locking mechanism substantially prevents the door from rotating in directions away from the lingual wall at each of the plurality of door positions.

45. The self-ligating bracket of embodiment 44, wherein the closed state includes an initial door position and a final door position, wherein the door is rotatable in an arc between the initial position and the final position, and wherein the locking mechanism substantially prevents the door from rotating in directions away from the lingual wall at any position of the door along the arc.

46. The self-ligating bracket of embodiment 44, wherein the locking mechanism inhibits the door from rotating more than 5 degrees in a backward arc in directions away from the lingual wall.

47. The self-ligating bracket of embodiment 46, wherein the locking mechanism inhibits the door from rotating more than 2 degrees in a backward arc in directions away from the lingual wall.

48. The self-ligating bracket of embodiment 47, wherein the locking mechanism inhibits the door from rotating more than 1 degree in a backward arc in directions away from the lingual wall.

49. The self-ligating bracket of embodiments 44-48 and including any aspect of embodiments 1-40.

50. The self-ligating bracket of embodiment 44, and further including a spring biasing the door in the direction of the archwire slot when the door is in the closed state.

51. The self-ligating bracket of embodiment 50, wherein the spring biases the door in the direction of the archwire slot at each of the plurality of closed door positions.

All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention which is defined by the following embodiments and their equivalents.

The invention claimed is:

1. A self-ligating orthodontic bracket comprising,
a base for bonding the appliance to a tooth surface;
a body extending outwardly from the base, the body defining an archwire slot extending in a mesial-distal direction across the body;
a hinge structure defining a first reference axis, the structure disposed on a first side of the archwire slot;
a door coupled to the hinge structure and rotatable about the first reference axis between an open state and a closed state, the door including a lingual surface and connected to the hinge structure, wherein an archwire is insertable into the archwire slot in the open state and the door retains the archwire in the archwire slot in the closed state; and
a locking mechanism engaging the door, impeding rotation of the door to the open state when the door is in the closed state, wherein the locking mechanism comprises a shaft extending in a facial direction relative to the base and engaging a lingual surface of the door, wherein, when the shaft is engaged with the lingual surface, attempted rotation of the door towards the open state compresses the shaft, preventing further rotation towards the open state, wherein the locking mechanism is on the first side of the archwire slot, and wherein the bracket lacks any other structure inhibiting rotation of the door towards the open state on the side of the archwire slot opposite the hinge structure.

2. The bracket of claim 1, wherein a portion of the lingual surface of the door is located in a gingival direction from the hinge structure.

3. The bracket of claim 1, further comprising a deflectable spring extending along at least a portion of the first reference axis.

4. The bracket of claim 3, wherein the door includes a strut extending from the lingual surface of the door and including a protrusion abutting the spring, and wherein the spring engages the protrusion to bias the door in the general direction of the base when the door is in the closed state and engages the protrusion to bias the door in the direction away from the base when the door is in the open state.

5. The bracket of claim 3, wherein the hinge structure and spring extend along axes that are generally parallel to the archwire slot.

6. A self-ligating orthodontic bracket comprising,
a base for bonding the appliance to a tooth surface;
a body extending outwardly from the base, the body defining an archwire slot extending in a mesial-distal direction across the body and including a lingual wall;
a hinge structure defining a first reference axis, the structure disposed on a first side of the archwire slot;
a door coupled to the hinge structure and rotatable about the first reference axis between an open state and a closed state, the door including a lingual surface and connected to the hinge structure, wherein an archwire is insertable into the archwire slot in the open state and the door retains the archwire in the archwire slot in the closed state; and
a locking mechanism engaging the door and disposed on the first side of the archwire slot, impeding rotation of the door to the open state when the door is in the closed state,
wherein the closed state comprises a plurality of door positions relative to the lingual wall, and wherein the locking mechanism substantially prevents the door from rotating in directions away from the lingual wall at each of the plurality of door positions.

7. The self-ligating bracket of claim 6, wherein the closed state includes an initial door position and a final door position, wherein the door is rotatable in an arc between the initial position and the final position, and wherein the locking mechanism substantially prevents the door from rotating in directions away from the lingual wall at any position of the door along the arc.

8. The self-ligating bracket of claim 7, and further including a spring biasing the door in the direction of the archwire slot when the door is in the closed state, and wherein the spring biases the door in the direction of the archwire slot at each of the plurality of closed door positions.

9. The self-ligating bracket of claim 6, wherein the locking mechanism inhibits the door from rotating more than 5 degrees in a backward arc in directions away from the lingual wall.

10. A self-ligating orthodontic bracket comprising,
a base for bonding the appliance to a tooth surface;
a body extending outwardly from the base, the body defining an archwire slot extending in a mesial-distal direction across the body;
a hinge structure defining a first reference axis;
a door rotatable about the first reference axis between an open state and a closed state, the door comprising one or more struts extending in the general direction of the base from a lingual surface of the door; and
a first spring offset from at least a portion of the hinge structure, wherein the first spring comprises a deflectable beam extending along a second reference axis that is substantially parallel to the first reference axis, wherein the first spring biases the door in the direction of the archwire slot when the door is in the closed state, and wherein the door includes a protrusion abutting the beam, and wherein the beam engages the protrusion to bias the door in the general direction of the base when the door is in the closed state and engages the protrusion to bias the door in the direction away from the base when the door is in the open state, and wherein opening the door causes a portion of the protrusion to move in a direction away from the base, whereby the beam is deflected.

11. The bracket of claim 10, further including a locking mechanism engaging a surface of the door, biasing the door towards the base in the closed state to impede rotation of the door to the open state, wherein the locking mechanism is on the first side of the archwire slot.

12. The bracket of claim 11, wherein the bracket lacks any other structure inhibiting rotation of the door towards the open state on the side of the archwire slot opposite the hinge structure.

13. A self-ligating orthodontic bracket comprising,
a base for bonding the appliance to a tooth surface;
a body extending outwardly from the base, the body defining an archwire slot extending in a mesial-distal direction across the body;
a hinge structure defining a first reference axis, the structure disposed on a first side of the archwire slot;
a door coupled to the hinge structure and rotatable about the first reference axis between an open state and a closed state, the door including a lingual surface and connected to the hinge structure, wherein an archwire is insertable into the archwire slot in the open state and the door retains the archwire in the archwire slot in the closed state; and
a locking mechanism engaging the door, impeding rotation of the door to the open state when the door is in the closed state, wherein the locking mechanism includes a lever arm extending in a generally occlusal-gingival direction from a portion of the shaft, the lever arm deflectable in the direction of the base to disengage the shaft from the door, wherein the locking mechanism is on the first side of the archwire slot, and wherein the bracket lacks any other structure inhibiting rotation of the door towards the open state on the side of the archwire slot opposite the hinge structure.

14. The bracket of claim 13, wherein the door includes a channel in a lingual surface, and wherein the lever arm is received in the channel.

15. The bracket of claim 13, wherein the lingual surface of the door includes a recessed area including a concave surface.

16. The bracket of claim 15, wherein the locking mechanism includes a rotation stop at an apex of the shaft, and wherein the stop is received in the recessed area of the lingual surface.

* * * * *